US011839728B2

(12) United States Patent
Tearney et al.

(10) Patent No.: US 11,839,728 B2
(45) Date of Patent: *Dec. 12, 2023

(54) TRANSNASAL CATHETER FOR IMAGING AND BIOPSYING INTERNAL LUMINAL ORGANS

(71) Applicant: The General Hospital Corporation, Boston, MA (US)

(72) Inventors: Guillermo J. Tearney, Cambridge, MA (US); Jing Dong, Malden, MA (US); David Odeke Otuya, Revere, MA (US); Yogesh Verma, Medford, MA (US); Hamid Farrokhi, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 793 days.

This patent is subject to a terminal disclaimer.

(21) Appl. No.: 16/607,493

(22) PCT Filed: Apr. 24, 2018

(86) PCT No.: PCT/US2018/029021
§ 371 (c)(1),
(2) Date: Oct. 23, 2019

(87) PCT Pub. No.: WO2018/200440
PCT Pub. Date: Nov. 1, 2018

(65) Prior Publication Data
US 2020/0139092 A1    May 7, 2020

Related U.S. Application Data

(60) Provisional application No. 62/488,917, filed on Apr. 24, 2017.

(51) Int. Cl.
A61M 25/10    (2013.01)
A61B 1/07     (2006.01)
(Continued)

(52) U.S. Cl.
CPC ......... A61M 25/10184 (2013.11); A61B 1/07 (2013.01); A61B 1/233 (2013.01);
(Continued)

(58) Field of Classification Search
CPC .... A61M 25/10184; A61B 1/07; A61B 1/233; A61B 5/0084; A61B 10/04
See application file for complete search history.

(56) References Cited

U.S. PATENT DOCUMENTS 4,311,146 A    1/1982  Wonder
4,651,753 A    3/1987  Lifton
(Continued)

FOREIGN PATENT DOCUMENTS

CN    1460029 A      12/2003
WO    2009086325 A2  7/2009
(Continued)

OTHER PUBLICATIONS

1) "Technique for Intraduodenal Placement of Transnasal Enteral Feeding Catheters" by Caulfield et al. Nutrition In Clinical Practice. 6:023-026. Feb. 1991. (Year: 1991).*
(Continued)

Primary Examiner — Jason M Ip
(74) Attorney, Agent, or Firm — QUARLES & BRADY LLP

(57) ABSTRACT

A catheter including an elongated tube having a channel; an inflatable chamber coupled to the elongated tube and in fluid communication with the channel; and a high-density liquid delivery system in fluid communication with the channel, the high-density liquid delivery system delivering a high-
(Continued)

density liquid to the inflatable chamber via the channel to cause the inflatable chamber to expand.

22 Claims, 22 Drawing Sheets

(51) Int. Cl.
*A61B 1/233* (2006.01)
*A61B 5/00* (2006.01)
*A61B 10/04* (2006.01)
*A61L 29/08* (2006.01)

(52) U.S. Cl.
CPC .......... *A61B 5/0066* (2013.01); *A61B 5/0084* (2013.01); *A61B 5/42* (2013.01); *A61B 10/04* (2013.01); *A61L 29/08* (2013.01); *A61M 2025/1043* (2013.01)

(56) References Cited

U.S. PATENT DOCUMENTS

| | | | |
|---|---|---|---|
| 4,961,738 A | 10/1990 | Mackin | |
| 5,248,312 A | 9/1993 | Langberg | |
| 5,380,276 A | 1/1995 | Miller | |
| 9,433,339 B2 | 9/2016 | Allyn | |
| 2003/0195504 A1* | 10/2003 | Tallarida | A61B 18/1492 606/41 |
| 2005/0240147 A1* | 10/2005 | Makower | A61B 10/06 623/1.11 |
| 2006/0247575 A1* | 11/2006 | Cartledge | A61M 25/10 604/102.01 |
| 2009/0171336 A1 | 7/2009 | Weber | |
| 2010/0097373 A1* | 4/2010 | Besz | A61J 15/0007 345/419 |
| 2010/0210937 A1 | 8/2010 | Tearney | |
| 2016/0030022 A1* | 2/2016 | Sheth | A61B 10/04 600/478 |
| 2016/0066896 A1 | 3/2016 | Abner | |
| 2017/0007203 A1 | 1/2017 | Courtney | |

FOREIGN PATENT DOCUMENTS

| | | |
|---|---|---|
| WO | 2012027641 A2 | 3/2012 |
| WO | 2012059082 A2 | 5/2012 |
| WO | 2014143459 A1 | 9/2014 |
| WO | 2019168634 A1 | 9/2019 |

OTHER PUBLICATIONS

China National Intellectual Property Administration. Notice on the First Office Action for application 201880041966.6, dated May 31, 2021. With translation.

International Searching Authority, International Search Report and Written Opinion for application PCT/US2018/029021, dated Jul. 16, 2018.

European Patent Office. Extended European Search Report for application 18791264.7, dated Dec. 1, 2020. 7 pages.

China National Intellectual Property Administration, Second Office Action and Search Report, Application No. 201880041966.6, dated Apr. 19, 2022, 16 pages.

China National Intellectual Property Administration, Third Office Action, Application No. 201880041966.6, dated Nov. 29, 2022, 9 pages [Partial English Language Translation].

China National Intellectual Property Administration, Decision on Rejection, Application No. 201880041966.6, dated Mar. 1, 2023, 8 pages [Partial English Language Translation].

European Patent Office, Communication Pursuant to Article 94(3) EPC, Application No. 18791264.7, dated Jun. 23, 2023, 7 pages.

* cited by examiner

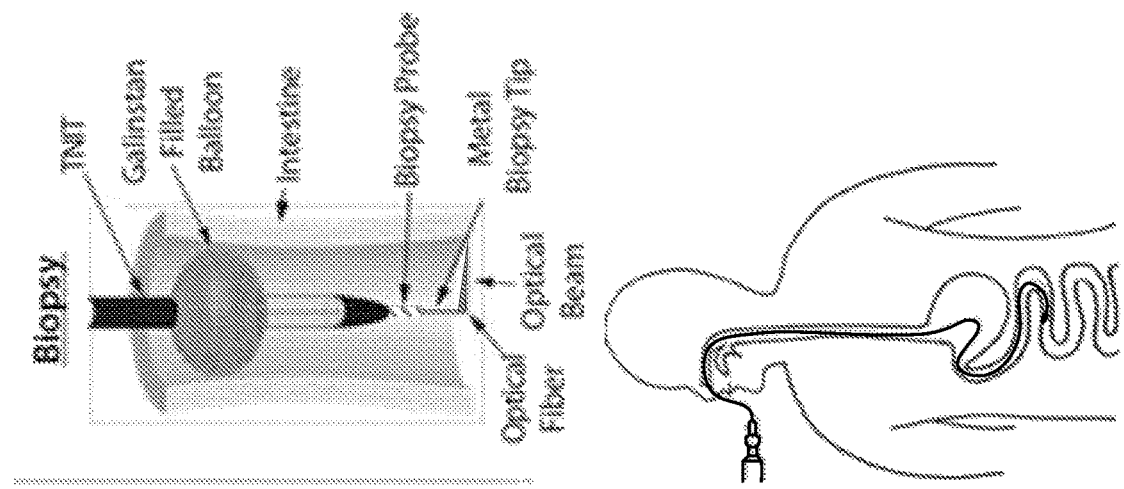
FIG. 1
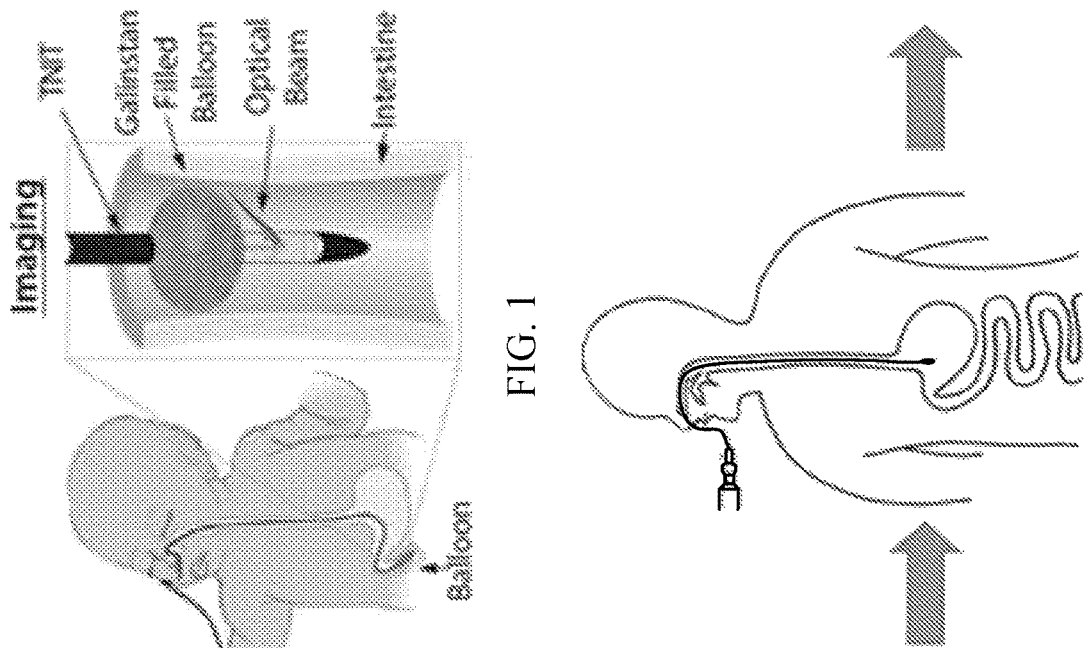
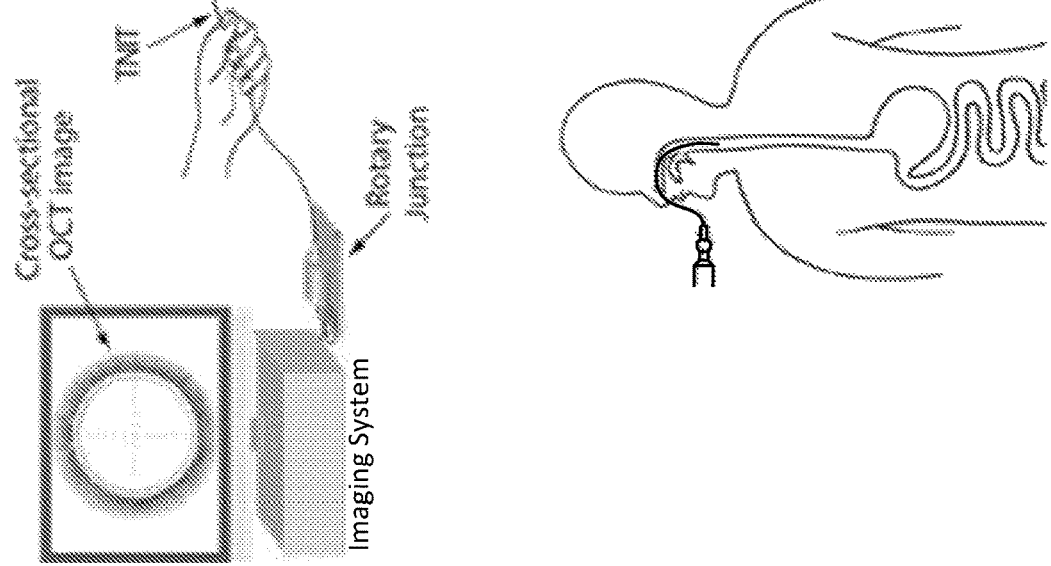
FIG. 2

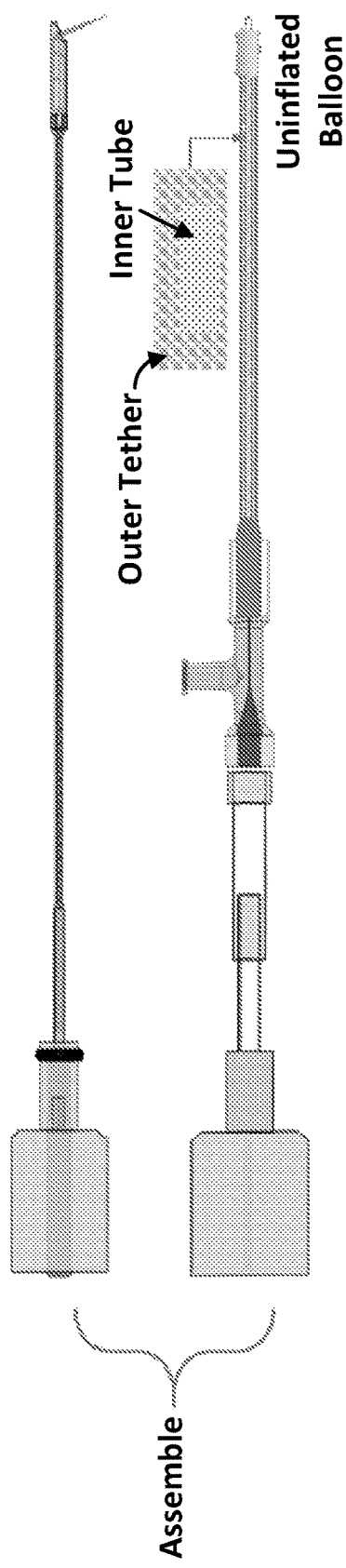
FIG. 3E1
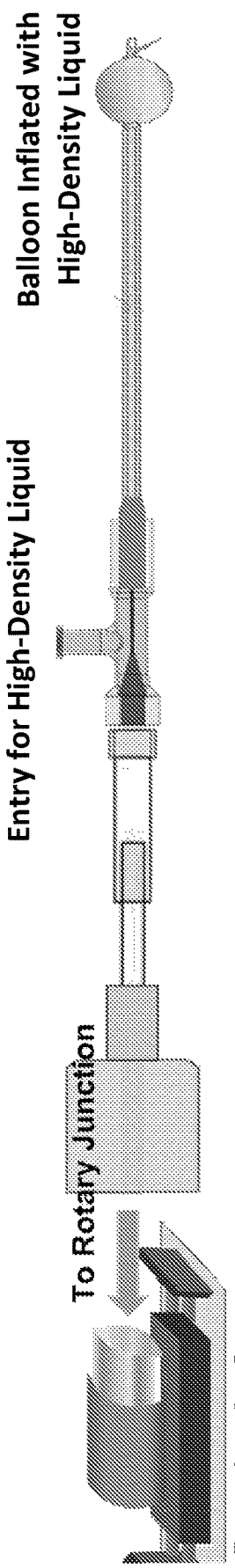
FIG. 3E2

| 602 | Proximal Inner Cap | 616 | Probe housing |
| 604 | E2000 Connector | 618 | Polished Ball lens |
| 606 | Coupler | 620 | Optical fiber |
| 608 | O ring | 622 | Spacer |
| 610 | Hypotube | | |
| 612 | Driveshaft | | |

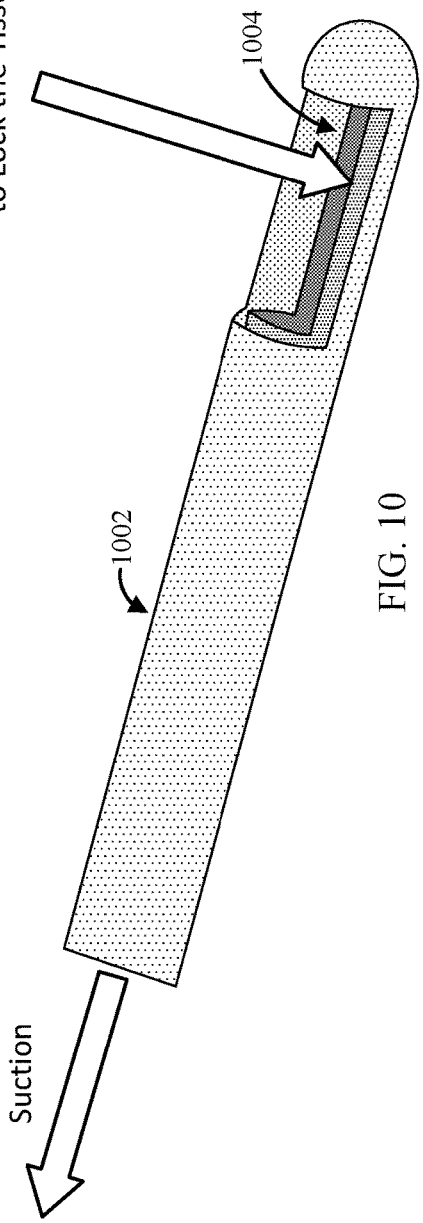
FIG. 10
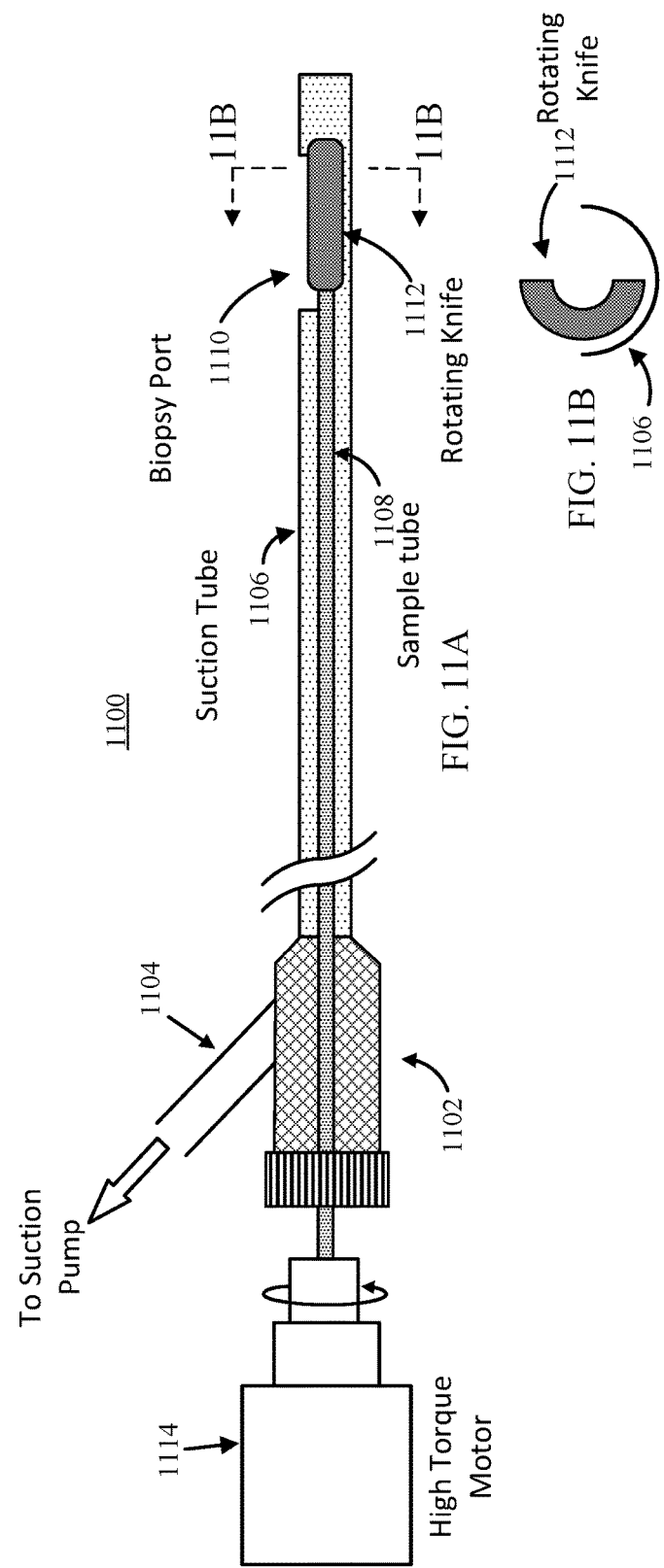
FIG. 11A
FIG. 11B

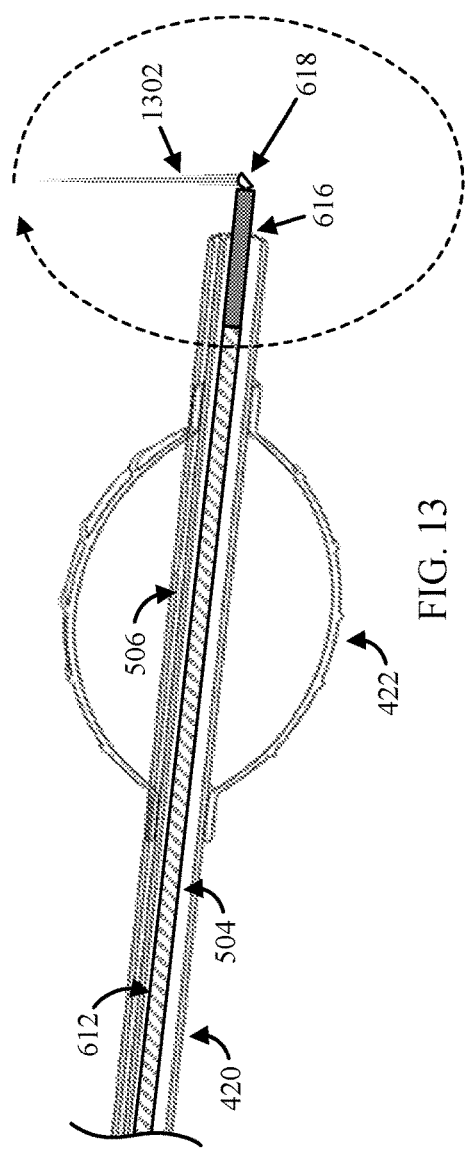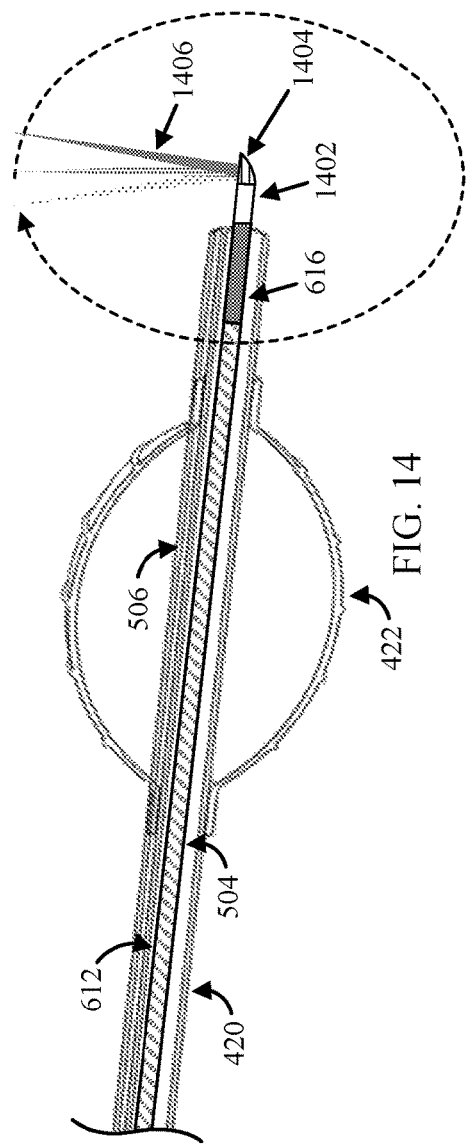

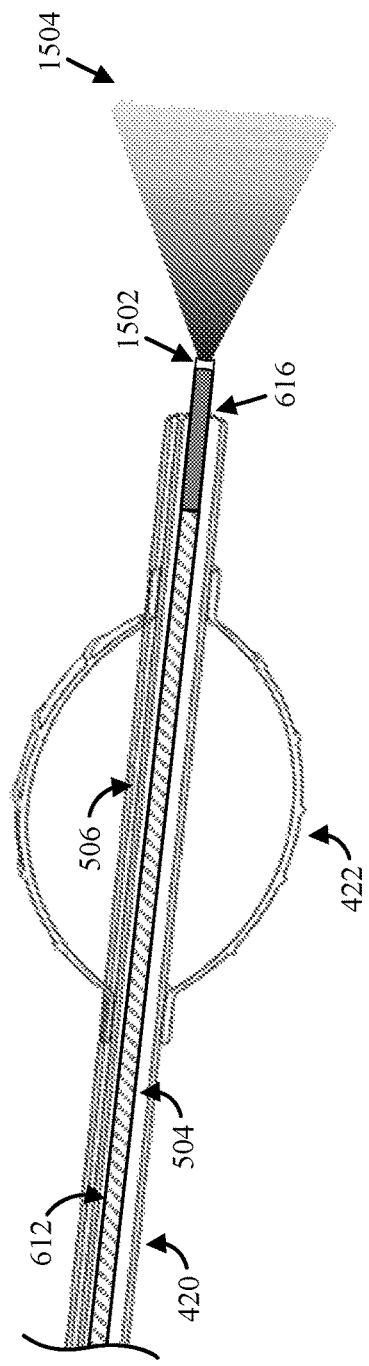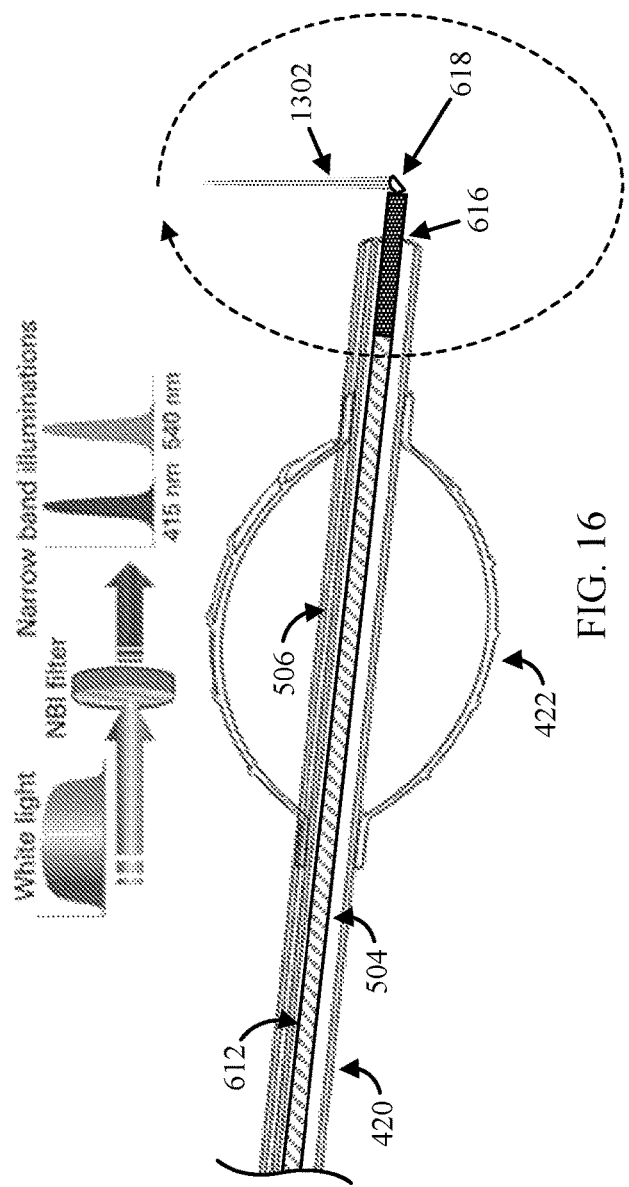
FIG. 15
FIG. 16

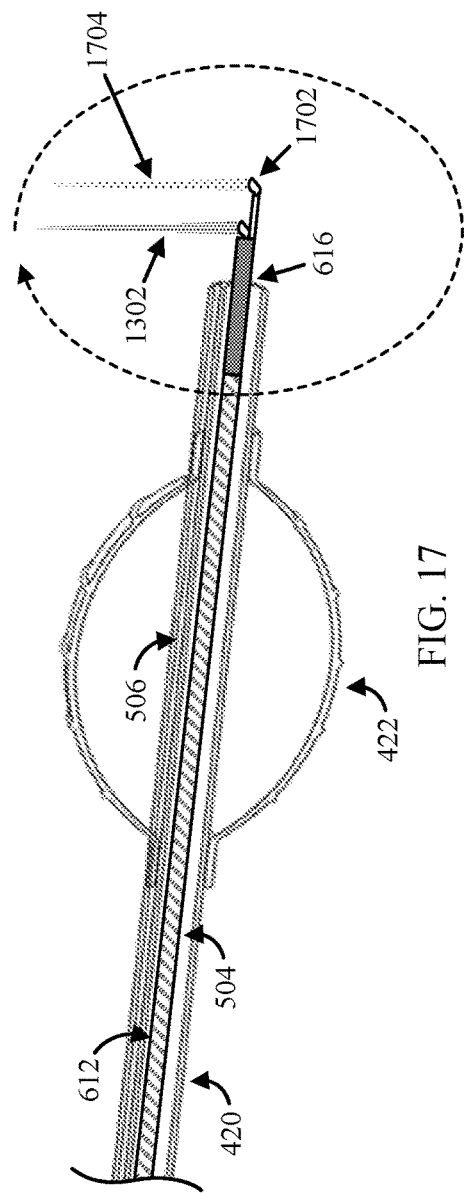
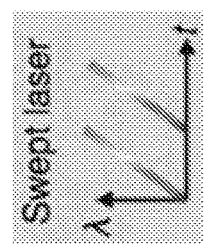
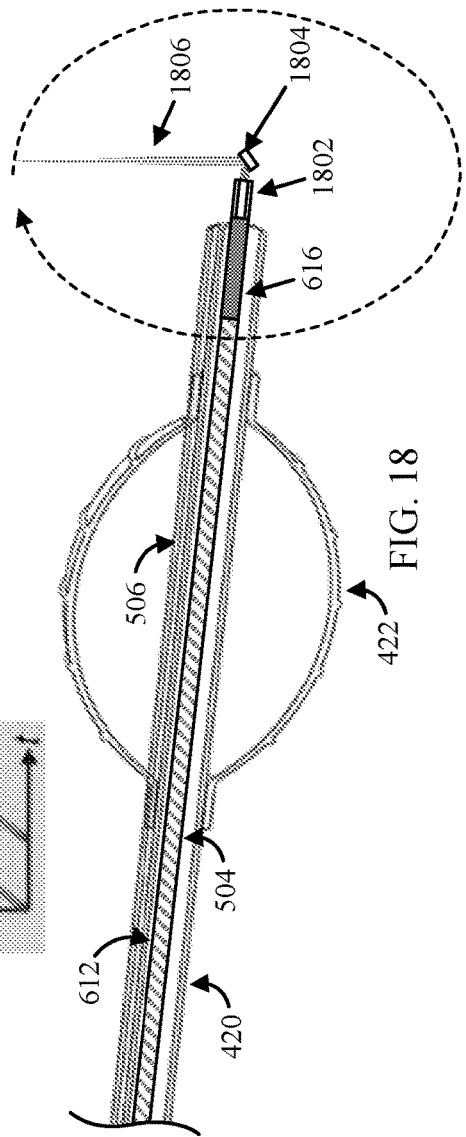
FIG. 17
FIG. 18

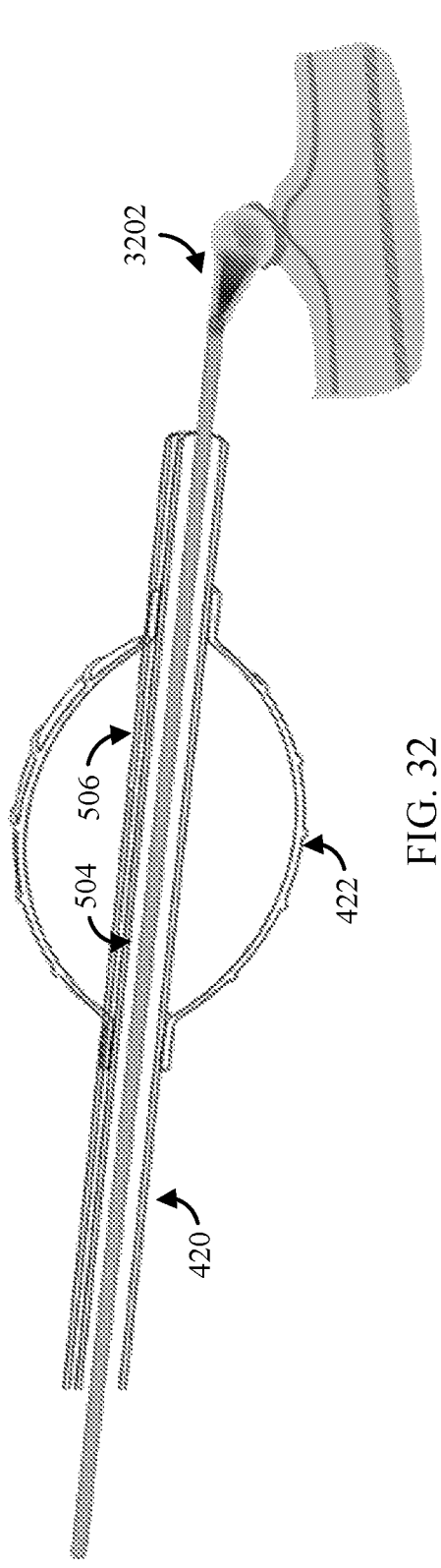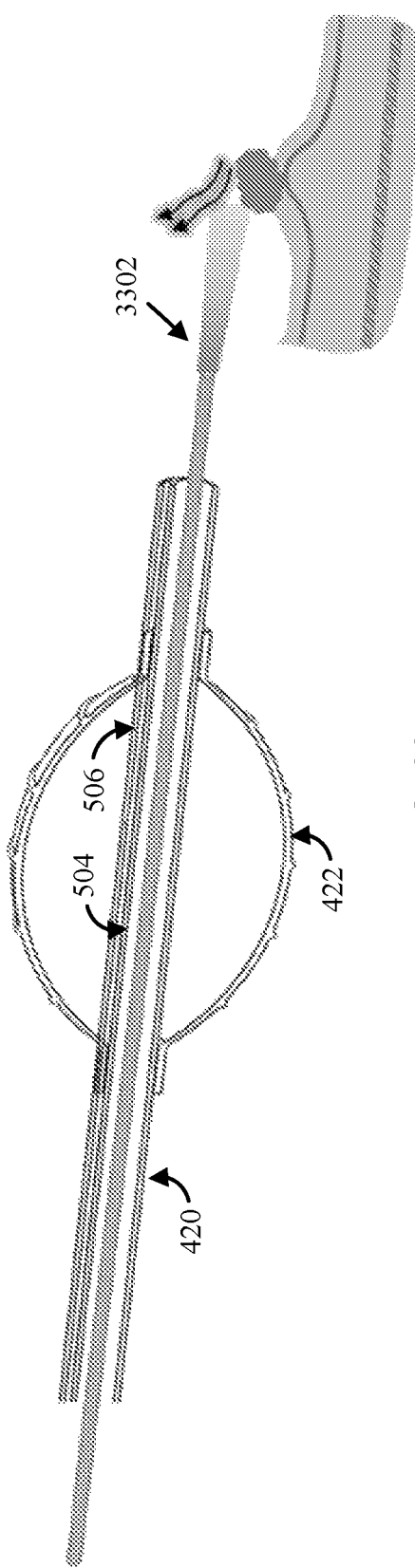
FIG. 32
FIG. 33

TRANSNASAL CATHETER FOR IMAGING AND BIOPSYING INTERNAL LUMINAL ORGANS

CROSS-REFERENCE TO RELATED APPLICATIONS

This application represents the national stage entry of PCT International Application No. PCT/US2018/029021 filed Apr. 24, 2018, which claims the benefit of U.S. Provisional Patent Application Ser. No. 62/488,917 filed on Apr. 24, 2017, and entitled "Transnasal Catheter for Imaging and Biopsying Internal Luminal Organs," which is incorporated by reference herein in its entirety.

FIELD OF THE DISCLOSURE

The present disclosure relates to apparatus and methods for providing access transnasally to luminal gastrointestinal spaces in subjects including infants, small children, and adults to obtain images and biopsy samples and to provide treatment, and more particularly to a catheter with an inflatable portion at a distal end thereof for providing such access.

BACKGROUND INFORMATION

Endoscopy is a standard technique for imaging, sampling tissue, and treating gastrointestinal tissue. Limitations of endoscopy include its invasiveness, frequently requiring that subjects who undergo the procedure be consciously sedated. Sedation necessitates that the endoscopy procedure be conducted in a specialized setting to mitigate complications should they arise. Patients undergoing this procedure must fully recover for them to return to their daily activities. Endoscopy is further problematic for infants, young children, and debilitated adults. These limitations of endoscopy motivate the alternative methods for GI tract diagnosis, sampling, and treatment that do not require conscious sedation.

SUMMARY OF THE INVENTION

Accordingly, in various embodiments the present invention provides an apparatus that can: 1) be non-invasively introduced and used in unsedated subjects, 2) obtain comprehensive images (e.g. white light or other microscopic images) from within the GI tract (e.g. intestinal epithelial microstructure) in vivo, 3) isolate targeted tissue biopsies for further processing for histopathological, molecular, genome, and microbiome analysis, and/or 4) be compatible for use in under-resourced settings. In certain embodiments, use of the apparatus does not require sedation of the subject, the apparatus can be delivered to a region of the GI tract (e.g. can be centered and traversed) by peristalsis, its use can be administered transnasally by trained personnel, it is inexpensive, and its operation can provide real-time imaging information.

While a tethered capsule imaging device would provide many of these advantages, it would be difficult to deliver existing capsules transnasally (e.g. through a nasogastric tube) due to their large size and thus there is a need to design an alternative "capsule" (i.e. an apparatus which provides the functions and benefits of a capsule) which can be administered transnasally, particularly in infants and small children. Among other features, such a "capsule" should have sufficient size and weight to enter the small intestine (e.g. passively) and in some cases be able to expand the small intestine and ultimately be able to capture and retrieve tissue samples from the small intestine. Nevertheless, such a device may be usable throughout the GI tract in a wide variety of subjects for diagnosing and treating a wide array of conditions.

Thus, in some embodiments the invention includes a catheter including an elongated tube having a channel; an inflatable chamber coupled to the elongated tube and in fluid communication with the channel; and a high-density liquid delivery system in fluid communication with the channel, the high-density liquid delivery system delivering a high-density liquid to the inflatable chamber via the channel to cause the inflatable chamber to expand.

In another embodiment the invention includes a method including: providing a catheter comprising an elongated tube having a first channel and a second channel, an inflatable chamber coupled to the elongated tube and in fluid communication with the first channel, and a high-density liquid delivery system in fluid communication with the first channel; and delivering, using the high-density liquid delivery system, a high-density liquid to the inflatable chamber via the first channel to cause the inflatable chamber to expand.

In yet another embodiment the invention includes a catheter including an elongated tube having a first channel and a second channel; an inflatable chamber coupled to the elongated tube and in fluid communication with the first channel; and a high-density liquid delivery system in fluid communication with the first channel, the high-density liquid delivery system delivering a high-density liquid to the inflatable chamber via the first channel to cause the inflatable chamber to expand.

The foregoing and other aspects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 1 shows a schematic of a transnasal catheter system according to embodiments of the invention;

FIG. 2 shows a schematic of the placement and inflatable chamber inflation process;

FIG. 3E1 shows an optical probe core (upper) and a TNIT (lower), and FIG. 3E2 shows an assembly of the optical core and the TNIT where the optical core is coupled to a rotary junction;

FIG. 10 shows a close-up view of an embodiment of a probe tip for a suction-based mechanical biopsy sampling probe;

FIGS. 11A and 11B show an embodiment of a suction-based mechanical biopsy sampling probe in which the distally-located cylindrical knife is coupled to a proximally-located motor; FIG. 12A shows an image of the esophagus showing clear visualization of the layered esophageal squamous architecture, including the epithelium (E), lamina propria (LP), muscularis mucosa (MM), submucosa (SM), and muscularis propria (MP). FIGS. 12B and 12C show villous architectural morphology that is characteristic of the duodenum, where arrows point to individual villi and the wall thickness of the sheath, demarcated by an asterisk (*), is approximately 125 µm;

FIG. 13 shows OCT probe access of the GI tract through the TNIT for imaging;

FIG. 14 shows SECM probe access of the GI tract through the TNIT for imaging;

FIG. 15 shows white light endoscopy probe imaging through the TNIT;

FIG. 16 shows a narrow band imaging probe being inserted through the TNIT;

FIG. 17 shows NIRS imaging through the TNIT probe;

FIG. 18 shows Raman Spectroscopy through the TNIT probe;

FIG. 32 shows a photodynamic therapy probe inserted through the TNIT;

FIG. 33 shows a photothermal healing probe inserted through the TNIT;

DETAILED DESCRIPTION OF EXEMPLARY EMBODIMENTS

Figure 3B:
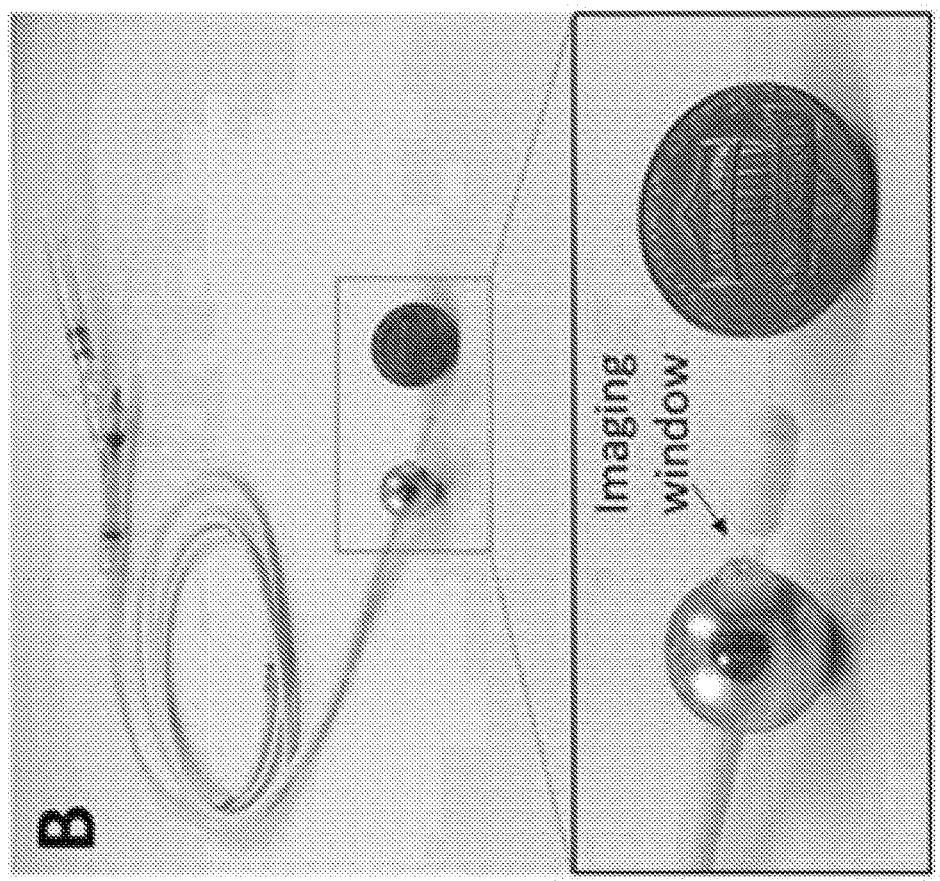
FIGS. 3A and 3B show an embodiment of a TNIT according to the invention with the attached inflatable chamber shown in the uninflated (FIG. 3A) and the inflated (FIG. 3B) states.

A significant challenge when imaging the infant intestine is the introduction of an imaging device. Endoscopy is not a viable option owing to its cost, complexity, and requirements for sedation/anesthesia. On the other hand, unsedated transoral introduction is technically challenging and may cause discomfort in infants.

Thus, in various embodiments an apparatus for gastrointestinal (GI) tract imaging is provided which uses an unsedated transnasal approach that is based on standard-of-care nasojejunal (NJ) tubes that are already in common use in young children and infants. Readily-available devices such as NJ tubes are low cost and easy to use by medical and trained nonmedical personnel and in some cases may even be placed in infants and children by their parents at home. Once placed in the GI tract, the bore of the NJ tube can serve as a port through which different instruments such as optical/imaging, treatment, and tissue/fluid sampling devices may be introduced. Although certain portions of the disclosure focus on use of the apparatus and methods in infant and small children, the disclosed apparatus and methods are applicable to subjects of various sizes and ages.

Accordingly, a transnasal endomicroscopy (TNEM) device has been developed which provides transnasal gastrointestinal tract access for imaging and other purposes. Embodiments of the device have been used in human clinical studies to successfully image the intestines of healthy adult subjects using unsedated, transnasal introduction. Given the roles of gut pathology and microbiota on the pathogenesis of many systemic diseases, the minimally-invasive gastrointestinal tract access afforded by this technology provides a significant breakthrough for medical research and health care across the globe.

FIG. 1 shows a schematic of a transnasal catheter system according to embodiments of the invention. The system includes a transnasal introduction tube (TNIT) that includes a modified NJ tube having an inflatable chamber (e.g. an elastic compartment such as a balloon) at its distal end (FIG. 1). In use, the inflatable chamber is inflated with a safe, high-density liquid (e.g. a liquid metal) when it is in the subject's stomach or other gastrointestinal space, at which point it passively transits through the pyloric sphincter and into the duodenum, the first section of the small intestine adjacent the stomach. After imaging, treatment, and/or biopsy are complete, the inflatable chamber is deflated (i.e. the high-density liquid is drawn out of the inflatable chamber) and the catheter is pulled back up through the pyloric sphincter so that the TNIT may be withdrawn through the nose. The insets on the right in FIG. 1 show the distal end of the TNIT with two different possible instruments protruding from the distal end, an imaging instrument (FIG. 1, left-hand "imaging" inset) or a biopsy instrument (FIG. 1, right-hand "biopsy" inset).

In certain embodiments, the transnasal catheter system may include an optical probe subsystem (OPS) for performing endomicroscopic imaging. The OPS may include an optical coherence tomography (OCT) endomicroscopy imaging probe coupled to a driveshaft-coupled optical fiber rotatably disposed within a channel in the TNIT. In various embodiments, probes designed for other optical techniques may be used instead of, or in addition to, OCT, including Spectrally Encoded Confocal Microscopy (SECM), µOCT, white light and narrow band imaging, near infrared spectroscopy (NIRS), Raman spectroscopy, and/or fluorescence imaging. For embodiments employing OCT, the OCT endomicroscopy imaging probe, located at a distal end of the OPS, may include microoptics (e.g. a ball lens) that focus and direct light towards the tissue (e.g. intestinal wall). The proximal end of the optical fiber of the OPS is connected to an optical rotary junction (RJ) that spins the driveshaft and in turn the optical fiber and OCT endomicroscopy imaging probe, scanning the beam around the circumference of the luminal organ. The RJ optically couples light from a stationary fiber emanating from the imaging system to the rotating fiber within the OPS.

Imaging with the OPS is generally performed during placement of the TNIT to ascertain that the device has entered the gastrointestinal tract and in particular the duodenum. After insertion, in certain embodiments additional steps may be taken to confirm that the TNIT was inserted correctly. This confirmation may be detected manually (e.g. based on imaging data) or may be automatically determined using a computer algorithm that can differentiate between anatomical differences of the layers of the esophagus and cartridge rings in the trachea. Manual or automatic confirmation of the TNIT position eliminates the need for the use of an additional imaging modality, such as x-ray, to confirm proper placement in the esophagus. Imaging may be started when the distal end of the probe reaches the stomach and continue until the distal end has reached the duodenum. FIG. 2 shows a schematic of the placement and inflatable chamber inflation process. As shown in FIG. 2, the TNIT may first be inserted transnasally (first panel), then it may be fed to the subject's stomach region where the inflatable chamber is inflated (second panel), and finally the TNIT with the inflated inflatable chamber is inserted into the small intestine (third panel). In general, the position of the TNIT catheter in the GI tract is manually controlled by a clinician or other trained operator.

In addition to imaging, use of the TNIT can also enable obtaining biopsy samples. Once the inflatable chamber has been positioned within the GI tract (e.g. intestine), in certain embodiments a biopsy probe may be inserted into a channel of the TNIT (FIG. 1) until a distal tip of the biopsy probe protrudes from the end of the TNIT. The biopsy probe may be inserted into a different channel of the TNIT than the OPS, or the OPS may first be removed and the biopsy probe may be inserted into the same channel. In some embodiments, the biopsy probe may also contain an integrated optical fiber which, when connected to the RJ and imaging system, emits and collects light from a distal end of the fiber to generate M-mode OCT images that can be used to determine when the biopsy probe is in contact with the tissue (e.g. the intestinal wall) (FIG. 1, right-hand "biopsy" inset). Once in contact, a biopsy is obtained which, in particular embodiments, may be performed cryogenically, e.g. the user may inject a coolant such as Freon into the biopsy probe to cool the tip, affixing frozen surrounding tissue to the biopsy device. The biopsy may then be retrieved by withdrawing the biopsy probe along with the attached tissue through the TNIT. Luminal contents can also be obtained by applying suction to the TNIT and mechanically removing a biopsy sample, as discussed further below.

Transnasal Introduction Tube (TNIT)

In one embodiment of a TNIT for use with adults, a commercially-available NJ tube with known functionality and biocompatibility was used; a length of NJ tube was provided so that it would reach the duodenum of an adult, which translates to a length of at least about 110 cm. For this particular embodiment, the outer diameter was specified to be around 9 French (9 F) in order to cause minimal discomfort in adults. Thus, a NJ tube meeting these criteria was a 125-cm long 9 F NJ tube made from silicone. For this particular embodiment, the tip was fashioned so that it contained an optically transparent image window near the distal tip, to allow passage of imaging light, and the distal tip of the tube was closed (see insets in FIGS. 3A, 3B). In some embodiments the tip may also include a cap (e.g. made of silicone) distal to the imaging window (FIGS. 3A, 3B) and particular embodiments the cap may include an opening through which an instrument such as an imaging probe and/or biopsy probe may project (FIG. 1, right-hand "biopsy" inset).

In other embodiments the TNIT may include one or more channels that are open at the distal end through which the instrument(s) (e.g. optical/imaging, treatment, and/or biopsy instruments) may protrude.

Figure 3A:
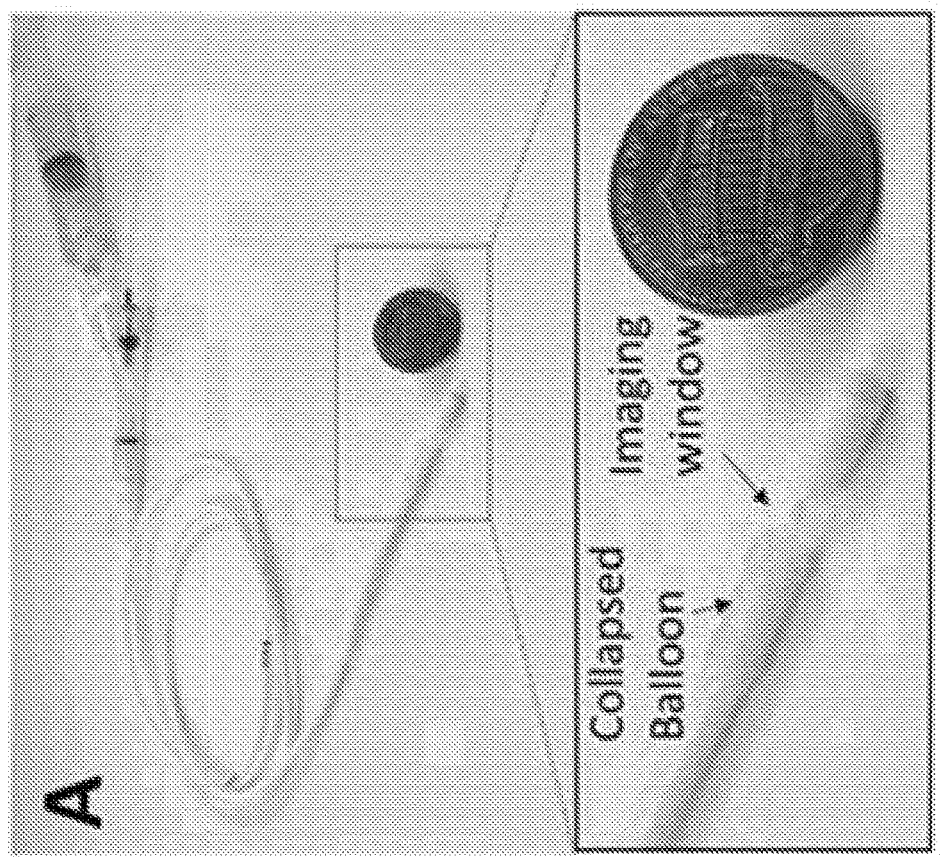
Figure 3C:
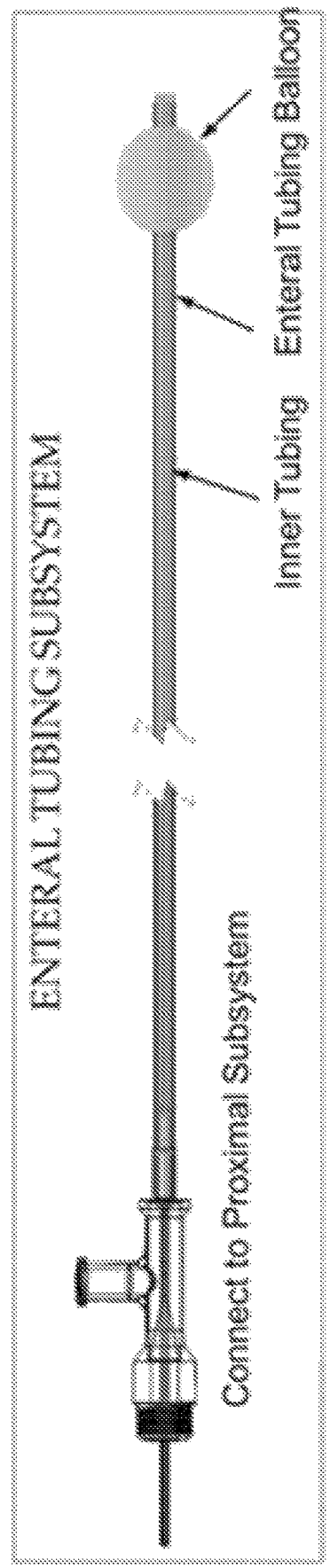
FIGS. 3C and 3D show an embodiment of a TNIT according to the invention in which the TNIT includes an Enteral Tube Subsystem (FIG. 3C) and a Proximal Subsystem (FIG. 3D)
Figure 3D:
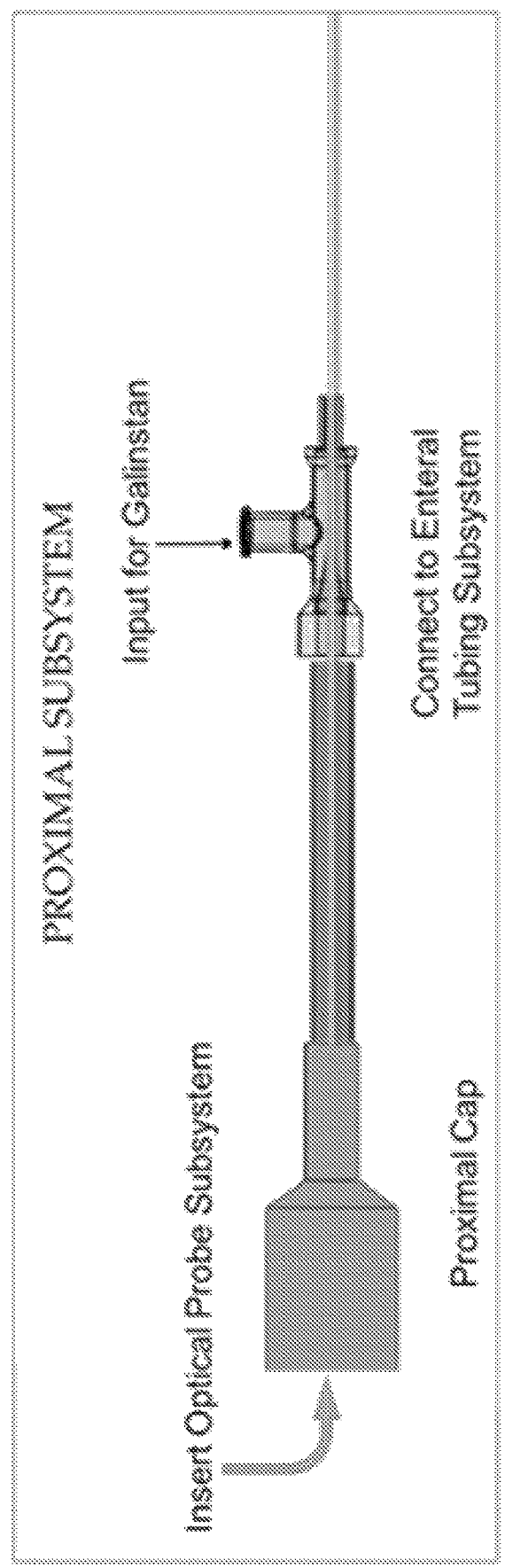

In various embodiments the TNIT may include an Enteral Tube Subsystem (FIG. 3C) and a Proximal Subsystem (FIG. 3D). The Enteral Tube Subsystem may include a channel used to deliver the high-density liquid (e.g. Galinstan) to inflate the inflatable chamber and an inner channel used to introduce instruments (e.g. an optical or biopsy instrument). The Proximal Subsystem may include a Y connector, a proximal cap, and/or a protection sheath for protecting any inserted instrument. FIG. 3E1 shows an embodiment of a TNIT with an optical probe inserted therein, including an optical probe core (upper) and a TNIT assembly (lower), and FIG. 3E2 shows an assembly of the optical core and the TNIT where the optical core is coupled to a rotary junction.

In certain embodiments the Enteral Tubing Subsystem, including the inflatable chamber, may be a single-use item and may undergo sterilization using ethylene oxide (EtO), which is the sterilization method for standard of care enteral tubes. In various other embodiments, Sterrad® may be used to sterilize the catheter. In general, all catheter materials that come in contact with the subject are biocompatible. Furthermore, embodiments of the device have been tested for resistance to low pH, tensile strength, and leakage, and follow the FDA guidance "Ingestible Telemetric Gastrointestinal Capsule Imaging System; Final Guidance for Industry and FDA."

Based on prior work with tethered intestinal capsules, it was determined that a capsule having a diameter of 11 mm allows circumferential imaging of the intestine and a capsule having a weight of ~6 grams facilitates transit of the capsule through the pylorus. Therefore, to obtain similar performance with the present device the inflatable chamber was designed so that, upon inflation, it would have an outer diameter and weight that are comparable to a capsule. Nevertheless, in other embodiments the diameter of the inflatable chamber upon inflation may range from 6 mm to 15 mm and the weight may range from 3 g to 12 g. Thus, in certain embodiments the diameter of the inflatable chamber upon inflation is at least 6 mm, at least 7 mm, at least 8 mm, at least 9 mm, at least 10 mm, at least 11 mm, at least 12 mm, at least 13 mm, at least 14 mm, or at least 15 mm. In certain other embodiments the weight of the inflatable chamber upon inflation is at least 3 g, at least 4 g, at least 5 g, at least 6 g, at least 7 g, at least 8 g, at least 9 g, at least 10 g, at least 11 g, or at least 12 g. In general, the weight and size of the inflatable chamber when it is inflated should be sufficient to facilitate passive translation through the particular portion of the GI tract (e.g. into the duodenum) for the particular subject. In various embodiments, an inflatable chamber was attached to the outer surface of the TNIT near the distal end, as shown in FIGS. 3A and 3B. The inflatable chamber in particular embodiments was made from an elastic sleeve (e.g. made of polyurethane or silicone) attached to the outer surface of the TNIT in a fluid-tight connection. In one particular embodiment a commercially-available silicone balloon, originally designed for a Foley catheter, was bonded to the NJ tube that was used as the TNIT tube in this embodiment. The Foley catheter balloons bonded well to the silicone NJ tube, withstanding pressure, acid, and temperature tests. In some embodiments relatively non-elastic materials (e.g. certain types of polyurethane) may be used for the inflatable chamber, such that the inflatable chamber is provided at its final size and such that, in the uninflated state, any extra material is wrapped around the TNIT.

Having produced an inflatable chamber attached to the TNIT, an additional feature for matching the performance of the capsule was to ensure that the inflatable chamber had sufficient weight (generally >3.0 g) to allow it to passively advance from the stomach to the duodenum under the force of gravity. Initially, a water/dextrose solution was used to inflate the inflatable chamber, but the density of this solution was not high enough to provide sufficient weight. Gallium was considered due to its high density and low viscosity. However, because its melting point is above room temperature, the possibility that it could solidify outside the body provided potential challenges for implementation. An alloy of gallium called Galinstan®, which includes gallium (Ga), indium (In), and tin (Sn), has a high density (6.44 g/cm$^3$ at 20° C.) and is a liquid at room temperature. Galinstan, which is already in use in infant thermometers, is considered to be a biologically safe material, and thus in certain embodiments is used for insufflation of the inflatable chamber (FIGS. 3A, 3B). In various embodiments, a high-density liquid with a density of at least 4.3 g/cm$^3$ would be sufficient to fill the inflatable chamber to 11 mm and provide a weight of greater than 3.0 g. In general, the high-density liquid may have a density of between 2.0-10.0 g/cm$^3$ and a viscosity of less than 0.003 Pa-s 20° C. and in a particular embodiment has a viscosity of about 0.0024 Pa-s at 20° C. (viscosity of Galinstan). In certain embodiments the high-density liquid may have a density of at least 2.0 g/cm$^3$, at least 3.0 g/cm$^3$, at least 4.0 g/cm$^3$, at least 5.0 g/cm$^3$, at least 6.0 g/cm$^3$, at least 7.0 g/cm$^3$, at least 8.0 g/cm$^3$, at least 9.0 g/cm$^3$, or at least 10.0 g/cm$^3$.

Figure 4:
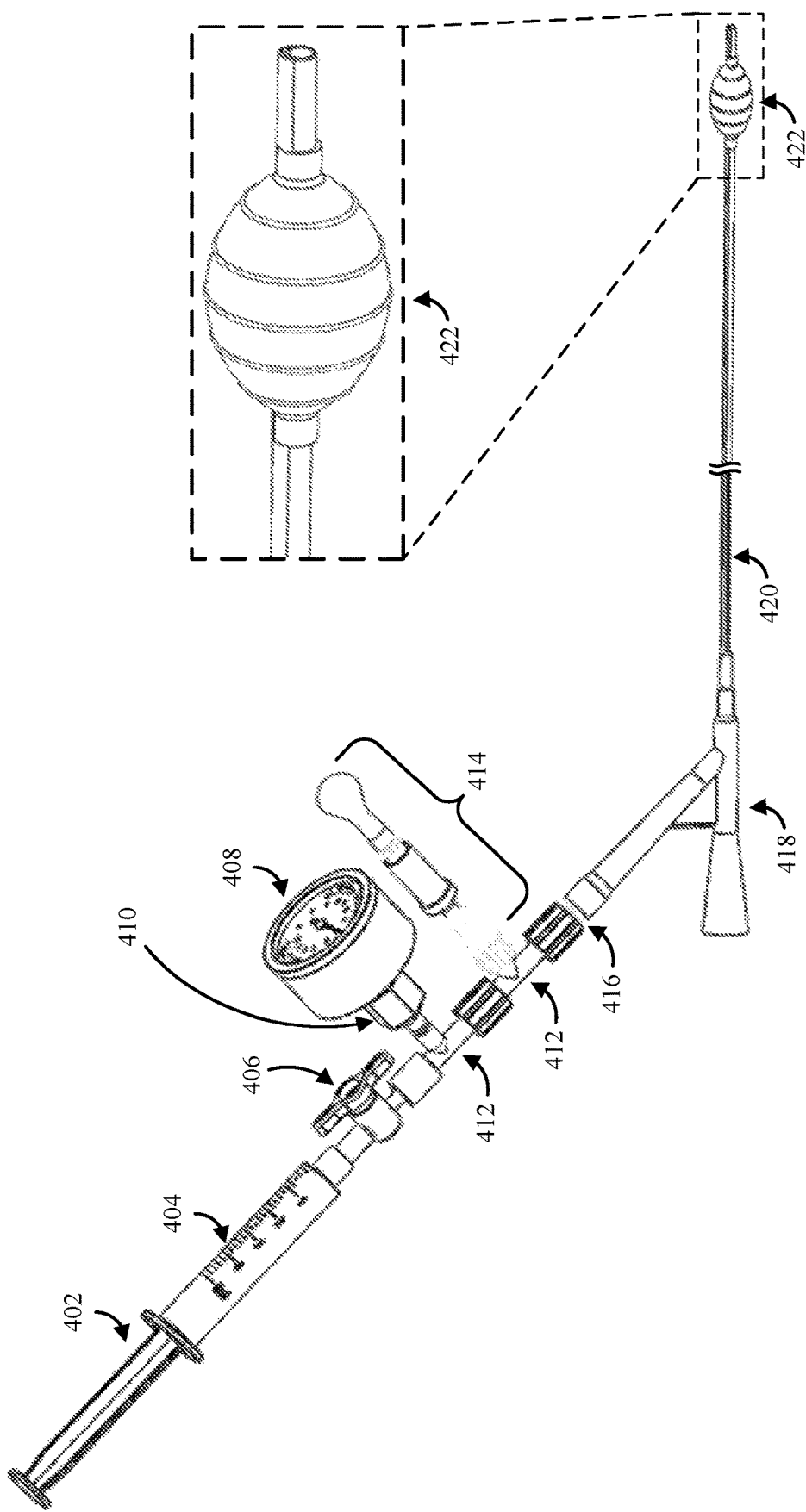
FIG. 4 shows a diagram of an embodiment of a high-density liquid delivery system, where the inset shows a close-up view of the inflated inflatable chamber at the distal end of the probe.

A proximally-located high-density liquid delivery system was designed for delivering the high-density liquid through the TNIT 420 to inflate the inflatable chamber (FIG. 4). In various embodiments, the high-density liquid delivery system includes a reservoir 404 for holding the high-density liquid (e.g. a syringe containing a liquid metal such as Galinstan), a valve (e.g. a stopcock), a pressure gauge 408, and a relief valve 414 (e.g. set to 15 psi or other suitable pressure level). The pressure gauge and/or the relief valve may be connected using T-connectors 412 and other suitable connectors 410, 416. The relief valve 414 may include a capture device (e.g. a finger cot as shown in FIG. 4) to collect any high-density liquid that escapes through the relief valve 414. The various instruments (e.g. imaging, treatment, and/or sampling/biopsy) may be coupled into the system using a Y-connector 418 that delivers the high-density liquid to a channel of the TNIT 420 and delivers one or more instruments to the appropriate TNIT channel(s). The components may be held together using suitable connectors such as barbed connectors, valves 406, or Luer lock connectors. The reservoir 404 may be filled with a particular amount of high-density liquid that has been determined to fill the inflatable chamber to a suitable level to provide the desired size (e.g. outer diameter) and weight properties. The pressure gauge 408 serves to monitor the inflatable chamber 422 pressure while it is deployed in vivo. In various embodiments the delivery of high-density liquid to and from the reservoir 404 may be automated, for example by a motorized pump mechanism that may deliver the high-density liquid to or from the inflatable chamber 422, e.g. under computer control, while pressure levels in the system are monitored, e.g. using a computer-controlled pressure monitor.

Figure 5B:
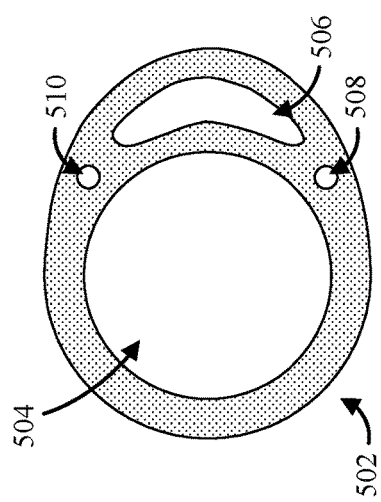
FIGS. 5A and 5B show diagrams of an embodiment of an extrusion for use with embodiments of a TNIT.
Figure 5A:
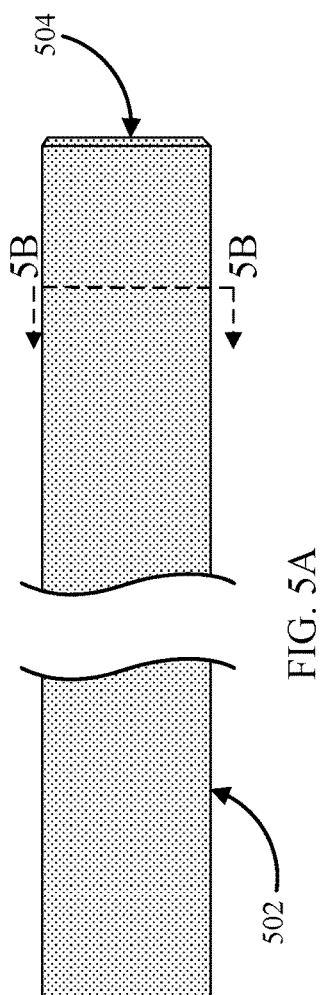

When pressure is applied to the reservoir 404 (e.g. using syringe plunger 402), the high-density liquid is forced into a channel in the TNIT 420 and ultimately into the inflatable chamber 422. As described above, in some embodiments a standard tube (e.g. a nasogastric (NG) tube or a NJ tube) may be used as a starting point for the TNIT 420. However, in certain embodiments the TNIT 420 may be custom-designed for use with the transnasal catheter system (FIGS. 5A, 5B). Thus, in various embodiments the TNIT may be generated from a custom-drawn tube extrusion so that the device can be made sufficiently small so as to be usable in infants and small children while still providing the necessary channels for high-density liquid and for instrumentation such as the OPS or a biopsy probe. Use of a custom-designed extrusion allows for maximization of the inner diameter of the inner channel (e.g. as a route for instrumentation to the distal end) while maintaining an outer diameter than is suitable for transnasal use in unsedated subjects such as infants. The cross-sectional profile of the custom TNIT extrusion may have an outer diameter that is approximately equal to that of a 6.5 F (2.17 mm) transnasal enteral tube that is commonly used in infants. A drawing of one particular embodiment of a custom designed TNIT is shown in FIG. 5A, with FIG. 5A showing a section 502 of the length of the TNIT extrusion and FIG. 5B showing a cross-sectional view of the TNIT extrusion.

In certain embodiments the custom extrusion may be made from various biocompatible materials (e.g. silicone or polyurethane) such as those currently used for standard enteral tubes. In the embodiment shown in FIGS. 5A and 5B, the TNIT's large main channel 504 or lumen (i.e. the channel having a circular cross-section in FIG. 5B) may serve as the port within which imaging, treatment, and/or biopsy probes can be inserted. The large main channel 504 or lumen of the embodiment of FIGS. 5A and 5B has an inner diameter of 1.5 mm, which allows the TNIT to accommodate instruments such as imaging or biopsy probes having outer diameters of up to 1.2 mm. In various embodiments, the crescent- or boomerang-shaped side lumen 506 may provide a separate channel for high-density liquid inflation of the TNIT's distal inflatable chamber by providing a fluid connection to the inflatable chamber. In particular embodiments, the extrusion may also include one or more smaller channels 508, 510 for other purposes. For example, the two smaller holes 508, 510 shown in FIG. 5B between the large lumen 504 and the high-density liquid channel 506 may be used for suction, air insufflation, and/or to hold wires/fibers for distal sensors (if needed). In various embodiments the TNIT may have an outer diameter ranging from 6 F (2 mm) to 12 F (4 mm), where the size used depends on the size of the particular subject; infants and small children would generally use smaller-diameter TNIT tubes, e.g. 9 F (3 mm) or smaller. In some embodiments the outer diameter of the TNIT is about 6 F, about 6.5 F, about 7 F, about 7.5 F, about 8 F, about 8.5 F, about 9 F, about 9.5 F, about 10 F, about 10.5 F, about 11 F, about 11.5 F, or about 12 F. In certain embodiments, larger TNIT tubes may accommodate additional larger channels and may have, for example, two or more channels (e.g. with circular cross sections) into which imaging, biopsy, and/or treatment instruments may be inserted, along with a channel for delivery of high-density liquid to the inflatable chamber. For those embodiments in which smaller- or larger-diameter TNIT tubes are used, suitable adjustments may be made to the various connectors (e.g. to the Y-connector 418) to accommodate the different-sized tubing.

The channel 506 or lumen of the TNIT that is used for high-density liquid delivery from the proximal end to the distal end for inflation of the inflatable chamber needs to be fluidly coupled to both the reservoir 404 and the inflatable chamber 422. In various embodiments, the inflatable chamber 422 may be made from a sleeve of elastic material (e.g. made of polyurethane or silicone) surrounding the TNIT tube 420 (FIG. 4). In some embodiments the inflatable chamber 422 in the deflated state may be flush with the outer surface of the TNIT tube so that the diameter of the inflatable chamber 422 (prior to inflation) is the same as the diameter of the TNIT. As noted above, in some embodiments the inflatable chamber 422 may be made of a relatively inelastic material that is wrapped around the TNIT 420 when it is not inflated.

For those embodiments in which the inflatable chamber 422 is made of a sleeve of material that surrounds the TNIT, an opening may be made on the outside of the TNIT (e.g. in the right-most wall of the channel 506 in FIG. 5B; see also opening 2102 in FIGS. 21-25) to provide a fluid connection to the channel 506 which carries the high-density liquid. In such embodiments, the high-density liquid channel 506 may be closed off at a point distal to the opening so that high-density liquid flowing through the TNIT channel must exit the TNIT into the inflatable chamber space to fill the inflatable chamber. A positive pressure is applied to the reservoir of high-density liquid to force the liquid into the inflatable chamber (e.g. to stretch the elastic material of the inflatable chamber into the larger inflated configuration) and in some embodiments the positive pressure may be maintained to keep the inflatable chamber in the inflated state. In other embodiments, a valve between the reservoir and the inflatable chamber may be closed in order to maintain the positive pressure in the inflatable chamber to keep it in the inflated state. The inflatable chamber expands radially outward (i.e. away from the long axis of the TNIT) when the high-density liquid is delivered. In various embodiments the inflatable chamber, when filled with high-density liquid, may be spherical (e.g. FIG. 3B), fusiform/spindle-shaped (e.g. FIG. 4 inset), "pill-shaped" (e.g. an elongated cylinder optionally having rounded ends), or other suitable shape.

To remove the high-density liquid and deflate the inflatable chamber, a negative pressure may be applied to the reservoir (e.g. by pulling the syringe piston for the embodiment of FIG. 4) to draw the high-density liquid back through the TNIT to the reservoir. Further, the elasticity of the inflatable chamber may contribute to deflation of the inflatable chamber instead of, or in addition to, application of negative pressure. Insofar as the initial inflation of the inflatable chamber stretches the elastic material of the inflatable chamber, the stretched inflatable chamber will tend to force out the high-density liquid once an opposing force such as the positive pressure from the reservoir is removed or reduced. Thus, even if the walls of the TNIT high-density liquid channel are not stiff enough to withstand negative pressure from the reservoir without collapsing, positive pressure from the stretched inflatable chamber may be sufficient to force the high-density liquid back to the reservoir to deflate the inflatable chamber.

At least one channel or lumen of the TNIT is sufficiently large to accommodate instruments such as an optical/imaging probe, a sampling/biopsy probe, or a treatment probe.

Optical Probe Subsystem (OPS)

In one embodiment an optical probe subsystem (OPS) may be provided which includes an optical probe for insertion into the TNIT coupled to additional components for obtaining data through the probe and processing the data, for example into one or more images.

In various embodiments, the OPS may be based on optical coherence tomography (OCT) principles, although, as noted above, in other embodiments probes designed for other optical techniques may be used instead of, or in addition to, OCT, including Spectrally Encoded Confocal Microscopy (SECM), μOCT, white light and narrow band imaging, near infrared spectroscopy (NIRS), Raman spectroscopy, and/or fluorescence imaging. OCT is an optical diagnostic method that provides high resolution microscopic images of internal structures of tissues in a noninvasive way. Because OCT light has limited penetration into the tissue, OCT probes are generally delivered directly to the organ of interest. Changes in refractive index in the sample cause the incident light to backscatter or reflect depending on the size of the objects with respect to the wavelength. The light returning from the tissue carries back information about its structure and is interfered with a portion of the light coming back from the reference arm. This signal is then detected, digitized, processed, and displayed on a computer screen as a one-dimensional axial profile of the refractive index changes (A-line), where larger changes in refractive index will result in higher contrast.

For two- (2D) and three-dimensional (3D) imaging of luminal organs using OCT, the optical beam must be delivered inside of the human body and continuously scanned over the length of the tissue to produce volumetric imaging. Intraluminal catheters that include an inner optical core deliver light from the imaging console outside of the patient to the tissue by means of an optical fiber terminated at the distal end with micro-optics. The micro-optics direct the optical beam to the side and focus the light on the tissue. In various embodiments, 2D circular scanning is implemented via a proximally-located rotary joint that continuously rotates the side-viewing optical core. Torque from an externally-located motor is delivered to the distally located optics using a torque coil (driveshaft) enclosing the optical fiber. The rotating core is enclosed in a static, protective outer sheath. Three-dimensional OCT of the entire length of the luminal organ can be acquired by simultaneous rotation and translation of the focused OCT beam, creating a helical pattern.

To obtain TNEM images in OCT-based embodiments, an optical probe coupled to a driveshaft-coupled optical fiber, which itself is rotatably disposed within a channel in the TNIT, sends and receives circumferentially-scanned OCT light from the tissue. In one particular embodiment, optics for the distal end of the optical fiber were designed to the following specifications, which were intended to mimic those used in tethered capsule endomicroscopy devices:

Spot size (resolution): <40 μm
Working distance: 4.5 mm with a depth of focus of more than 2 mm
Astigmatism: <20% difference in x and y plane
Non-uniform rotational distortion (NURD): <20% of circumference
Optical throughput: >70%

Figure 6A:
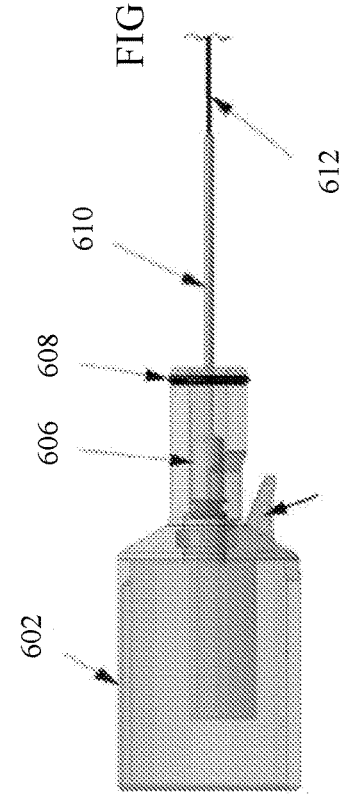
FIGS. 6A, 6B, and 6C show diagrams of an optical probe for use with embodiments of the optical probe subsystem.
Figure 6B:
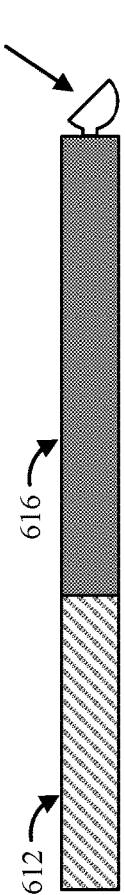
Figure 6C:
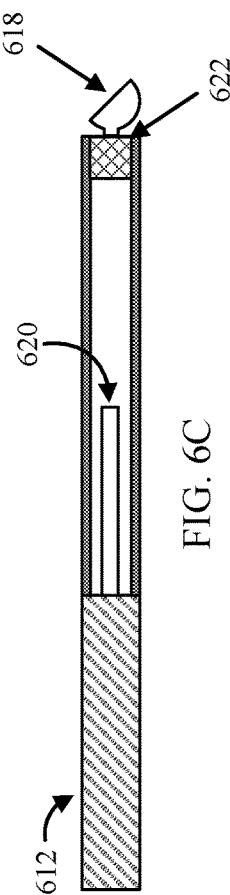

A particular embodiment of a design of the OPS is illustrated in FIGS. 6A-6C. In this embodiment the OPS includes a single-mode optical fiber 620 that is housed inside a driveshaft 612, which in turn may be located within hypotube 610 (FIG. 6A). The optical fiber is terminated at its distal end 614 by a housing 616 including a glass spacer 622 and coupled to a ball lens 618 that is polished to direct the focused beam towards the gastrointestinal tract wall (FIGS. 6B, 6C). The proximal end of the OPS is connected to a RJ that turns the driveshaft 612 and optical fiber 620 to effectuate circumferential scanning; in some embodiments the distal end 614 of the TNIT may include a clear optical window through which imaging may be performed (see FIGS. 3A, 3B). A three-layer torque-coil driveshaft with a thin layer of a low-friction coating (e.g. PTFE) on the inner surface may be used to minimize non-uniform rotational distortion (NURD). A high performance optical connector 604 (e.g. E2000™) with a low insertion loss is housed within cap 602 along with coupler 606 and is utilized to connect the OPS to the rotary junction to achieve high optical throughput.

The OPS includes a RJ to spin the optics at the distal end of the catheter. In some embodiments a RJ with increased optical throughput may be provided. The optical joint may be an off-the-shelf rotary joint (e.g. from the MJP series made by Princetel, Hamilton, NJ). In particular embodiments, this RJ will be specified for an operating wavelength of 1310 nm and a speed of 3000 rpm. The rotary mechanics may include a gear- or belt-driven drivetrain operated using a DC/BLDC motor, which will operate in the 12 VDC range and will be controlled via an enclosed motor controller with closed-loop speed control. The speed will be fine-tuned in such a way as to minimize rotational drift. The probe interface will utilize a high-precision, actively-aligned connector with a snap-on cap 602 design (connector shown in FIG. 6A), which may include an O-ring 608 for interfacing with a mating coupler, e.g. on the Y-connector 418. Power may be provided by the imaging system or an external outlet.

In various embodiments the transnasal catheter system may include an imaging system which connects to an optical or biopsy probe to deliver and receive light from a sample (e.g. a luminal sample such as the gastrointestinal tract wall) along with components that send and receive optical signals to the probe and process the optical signals to provide information about the sample (e.g. a luminal sample such as the duodenum), including one or more images. The imaging system in various embodiments may be compact and can be easily transported to sites anywhere in the world. In certain embodiments the imaging system may include a swept-source OCT (SS-OCT) system, which is a well-developed and mature imaging technology. Nevertheless, other imaging technologies may be used through a TNIT, including spectral-domain OCT (SD-OCT) (described below). In various other embodiments, higher resolution imaging technologies such as spectrally-encoded confocal microscopy (SECM), high-definition OCT (HD-OCT), and 1-μm-resolution OCT (μOCT) may be implemented using a TNIT to obtain higher resolution and greater image detail. In various embodiments, the OPS may be connected to a compact imaging system that provides the optics and power needed for imaging.

Table 1 lists specifications of one particular embodiment of a TNEM device which includes an OCT-based optical probe.

TABLE 1

Specifications for a TNEM device

| Parameter | Typical Value | Unit |
|---|---|---|
| Light transmission | Single Mode Fiber | — |
| Light transmission range | 1310 +/− 80 | nm |
| Transversal Resolution at 1310 nm | 25-40 | μm |
| Working distance from optics | <4 | mm |
| Scanning orientation | Side-viewing | — |
| Scanning speed | 20-40 | Hz |
| Catheter Length | 2 | m |
| Max. Outer diameter (including inflated chamber) | <13 | mm |

Biopsy Probe

In one embodiment a biopsy may be obtained using one of several different types of biopsy probes including a cryogenic biopsy probe or a suction-based mechanical biopsy sampling probe. In certain embodiments, either type of biopsy probe may include an optical fiber as described above which can obtain location information (e.g. M-mode OCT images) for determining when the probe is in contact with the tissue; in other embodiments in which the TNIT includes at least two channels large enough to accommodate instruments, a biopsy probe may be inserted into one channel and an imaging probe may be inserted into another channel to monitor the biopsy procedure. Briefly, a cryogenic biopsy probe may include a channel for delivering a coolant to the probe tip so that a sample may be obtained by freezing tissue onto the tip and removing the attached tissue. In use, the user may inject a coolant such as Freon into the biopsy probe to cool the tip, affixing frozen surrounding tissue to the biopsy device. The biopsy may then be retrieved by withdrawing the biopsy probe along with the attached tissue through the TNIT (FIG. 1, right-hand "biopsy" inset). Embodiments of cryogenic biopsy probes are disclosed in U.S. Application No. 62/637,517, filed Mar. 2, 2018, entitled "Devices, Systems, and Methods for Cryogenic Biopsy Sampling," which is incorporated by reference herein in its entirety.

Figure 7:
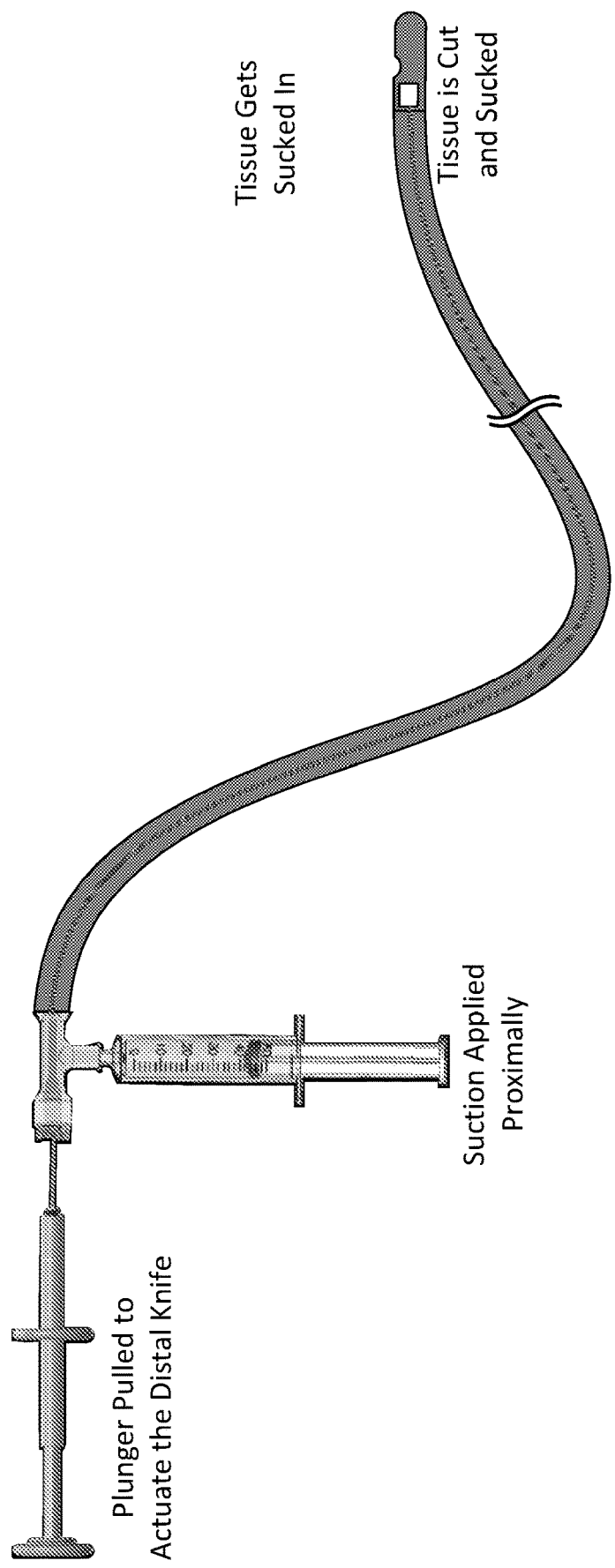
FIG. 7 shows an embodiment of a suction-based mechanical biopsy sampling probe.

In certain embodiments the biopsy probe may be a suction-based mechanical biopsy sampling probe (FIGS. 7-11). In general, a suction-based mechanical biopsy probe uses suction to draw a tissue sample into the probe tip and then removes the tissue sample, for example using a knife such as a rotating cylindrical knife to cut the tissue sample from the luminal surface. The excised sample may then be removed along with the biopsy probe (i.e. when the biopsy probe is withdrawn from the TNIT). FIG. 7 shows an embodiment of a suction-based mechanical biopsy sampling probe which includes a plunger at the proximal end of the probe that is coupled to a cylindrical knife at the distal end of the probe. Also at the proximal end of the probe is a suction device (e.g. a syringe) coupled to the probe tubing so that suction generated at the proximal end of the device is transmitted to the distal end. In general the suction is transmitted through the biopsy probe tubing, for example through a central channel which may also house a pull wire that couples the plunger to the cylindrical knife (see FIGS. 11A, 11B).

Figure 8:
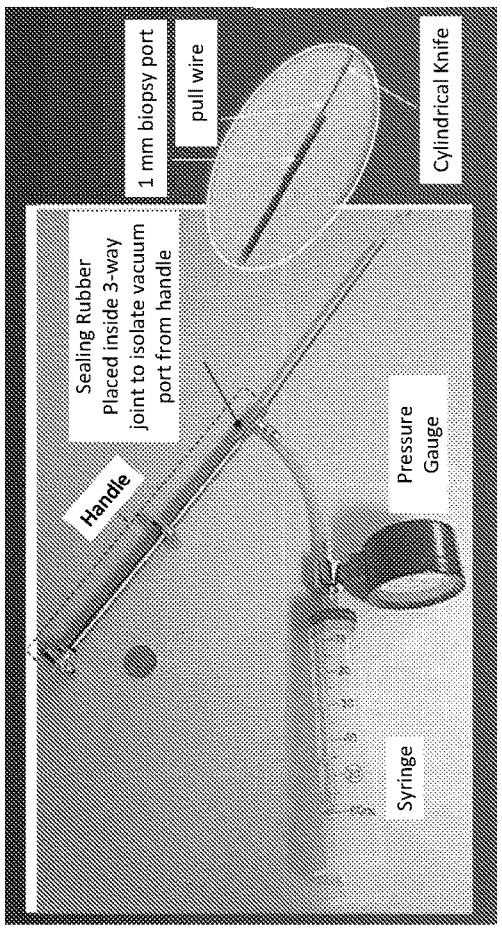
FIG. 8 shows another embodiment of a suction-based mechanical biopsy sampling probe and a close-up view of the cylindrical knife at the end of the probe.
Figure 9:
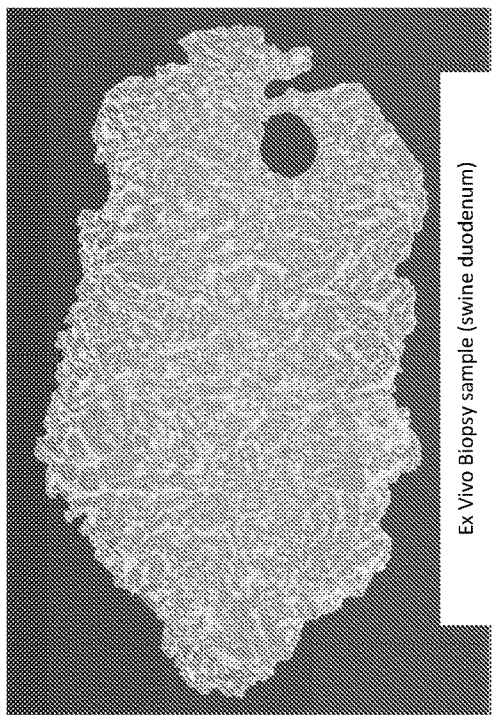
FIG. 9 shows a stained sample of tissue from swine duodenum that was obtained using such a probe.

FIG. 8 shows another embodiment of a suction-based mechanical biopsy sampling probe. As shown in FIG. 8, the suction device in this embodiment may also have a pressure gauge coupled thereto to monitor the pressure levels in the system. The inset in FIG. 8, which corresponds to the distal end of the probe, shows the cylindrical knife at the end of a pull wire protruding from the distal end of the biopsy probe tubing (which in this embodiment has an outer diameter of 1 mm); the pull wire is coupled to the plunger at the proximal end of the probe. FIG. 10 shows a close-up view of a distal end of a probe with a rotatable cylindrical knife 1112 disposed within the probe tip 1002. The probe tip 1002 in this embodiment is a cylindrical tube with a hemispherical rounded portion at the distal end and an open portion 1004 near the distal end. The cylindrical knife 1112 is located within the open portion 1004 so that a tissue sample that is drawn into the open portion 1004 of the probe tip 1002 (e.g. by suction) can be engaged by the cylindrical knife 1112, which is remotely driven by the plunger at the proximal end of the probe. FIG. 9 shows an example of a biopsy sample removed using such a probe (from swine duodenum). FIGS. 11A, 11B show another embodiment of a suction-based mechanical biopsy sampling probe 1100 in which the proximal end of the pull wire 1108 is attached to a high torque motor 1114 which rotates the pull wire 1108, which in turn rotates the cylindrical knife 1112. FIG. 11B shows a cross-section through the cylindrical knife 1112 at the line 11B-11B in FIG. 11A. The embodiment of FIGS. 11A, 11B includes a suction tube 1106 connected at the proximal end to a suction pump through a branch 1104 of a coupler 1102. The suction tube 1106 is coupled at the distal end to an opening 1110 where the cylindrical knife 1112 is located (FIG. 11A).

Figure 12:
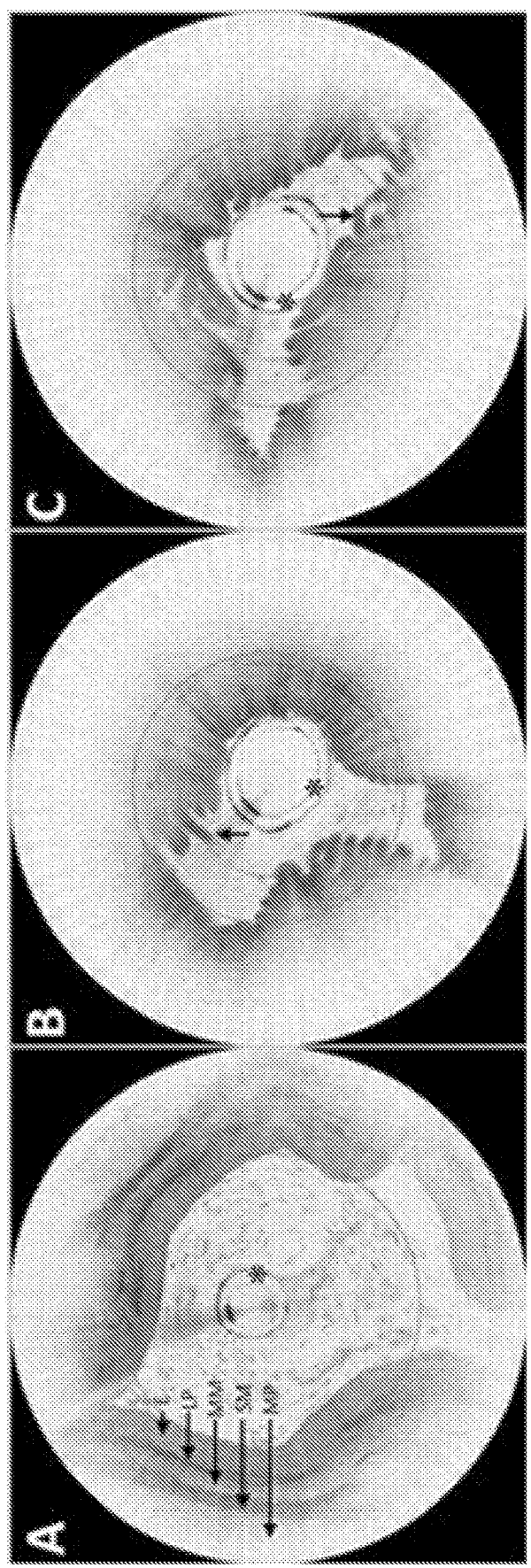
FIGS. 12A, 12B, and 12C show circumferential, cross-sectional TNEM images of the gastrointestinal tract obtained from an unsedated human subject in vivo.

After developing and validating a prototype of a TNEM device, initial studies with adult volunteers were approved by the appropriate IRB. The results of this study provide proof of concept and demonstrates safety in normal adults. The TNEM was used to image the duodenum of three healthy, non-sedated adult subjects (mean age, 23.3 yo) and the average duration of the procedures was 1.83 hours from device insertion to removal. Images produced by TNEM were comparable to those obtained by tethered capsule endoscopy (TCE) (FIGS. 12A-12C). In the esophagus, all of the architectural layers of squamous mucosa could be identified including the epithelium (E), lamina propria (LP), and muscularis mucosa (MM) (FIG. 12A). The submucosa (SM) and muscularis propria (MP) were also clearly seen (FIG. 12A). Copious intestinal villi (arrows in FIGS. 12B, 12C) were visualized throughout the duodenum.

While images produced by TNEM were generally comparable to those obtained by TCE, there were some differences between data obtained by TNEM and by TCE. The primary difference was that, since there was no capsule, the GI tract wall collapsed around the TNIT's imaging window. This caused the lateral resolution to be reduced because the tissue was closer to the imaging window than anticipated and the tissue was therefore slightly out of focus. In various embodiments this can be addressed by angling the imaging beam towards the inflatable chamber so the organ or tissue can be imaged in its distended state (FIG. 1, left-hand "imaging" inset).

As described below, various probes may be inserted through the one or more channels of the TNIT to provide diagnosis, sampling, or treatment of one or more regions of the GI tract of a subject:

Diagnosis

One of the applications for the inner lumen of the TNIT is medical diagnosis. Different imaging probes can be inserted through the lumen to image the GI tract. For this use, the TNIT would have a single or multiple lumen for balloon inflation and another lumen used as a working channel for imaging. Imaging could be performed through the TNIT protruding imaging window, or outside the distal end. To improve imaging, additional lumen may be present to inflate the intestines with air.

Optical Coherence Tomography (OCT)

The working channel of the TNIT 420 could be used as an access portal for OCT imaging which provides real time microstructural information of the GI tract (FIG. 13). The probe is inserted through the working channel of the TNIT and rotated to scan the GI tract wall via beam 1302. While the OCT probe rotates, the TNIT in combination with the OCT probe are retracted to capture the volumetric image.

Spectrally Encoded Confocal Microscopy (SECM)

The working channel of the TNIT could also be used as an access portal for SECM imaging which scans the sample in one dimension without moving parts by using wavelength swept source illumination and a diffraction grating 1404 at the back plane of the objective (GRIN) lens 1402 to produce a spectrally-tilted beam 1406 (FIG. 14). The probe is inserted through the working channel of the TNIT 420 and rotated to scan the GI tract wall. While the SECM probe rotates, the TNIT 420 in combination with the SECM probe are retracted to capture the entire enface microstructures of the GI tract.

White Light and Narrow Band Imaging

A miniature endoscope camera or fiber bundle could be inserted through the working channel of the TNIT. Such a probe having a lens 1502 at it end could emit broadband light 1504 (e.g. from an LED source) that would help provide bright field imaging of the lumen wall, which can be used for preliminary screening of lesions and suspicious structures (FIG. 15). Narrow band imaging could also be used to improve the scanning detail by using narrowly filtered blue and green wavelengths to generate a beam 1302 to scan a sample (FIG. 16). Endoscopy through the TNIT, compared to the standard of care, would not require sedation and would be lower cost.

Near Infrared Spectroscopy (NIRS), Raman Spectroscopy, and Fluorescence Imaging

Figure 19:
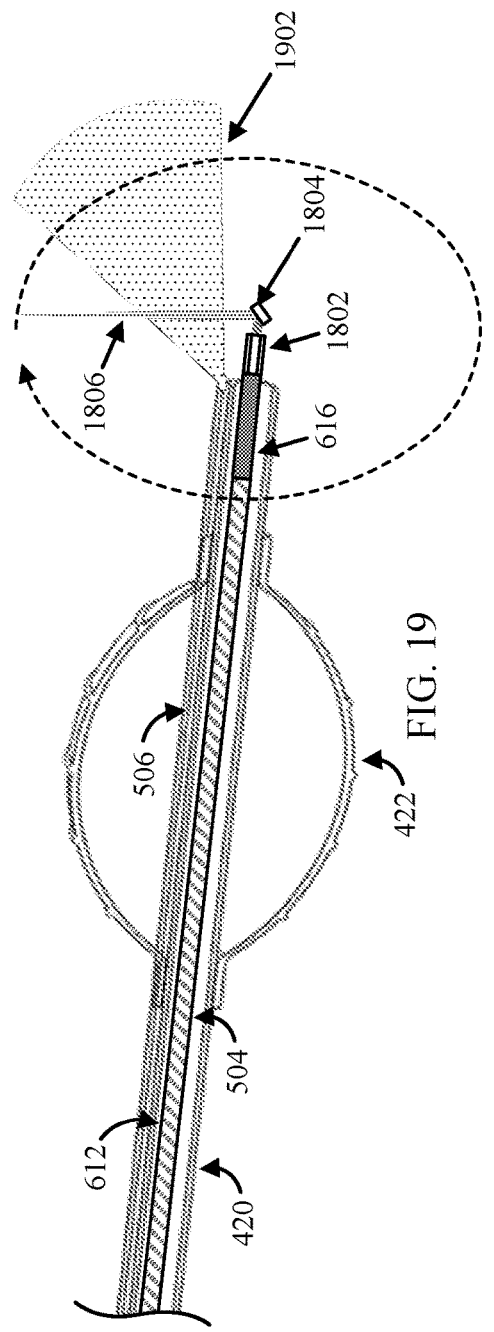
FIG. 19 shows fluorescence imaging and fluorophore spray through the TNIT.

The TNIT could also be used for dual modality (OCT and NIRS) imaging (FIG. 17, which may include detection fiber 1702 and NIRS signal beam 1704) and Raman Spectroscopy (FIG. 18, which may include double-clad fiber 1802 and mirror 1804 to generate scanning beam 1806) to provide structural and molecular composition of the GI tract. Fluorescence imaging can also be used by adding another channel in the TNIT for spraying a fluorophore (FIG. 19, showing fluorescence dye spray 1902). All three imaging modalities are potential candidates for increased sensitivity of early cancer screening compared to standard of care.

Gas/Temperature/pH Sensor

Figure 20:
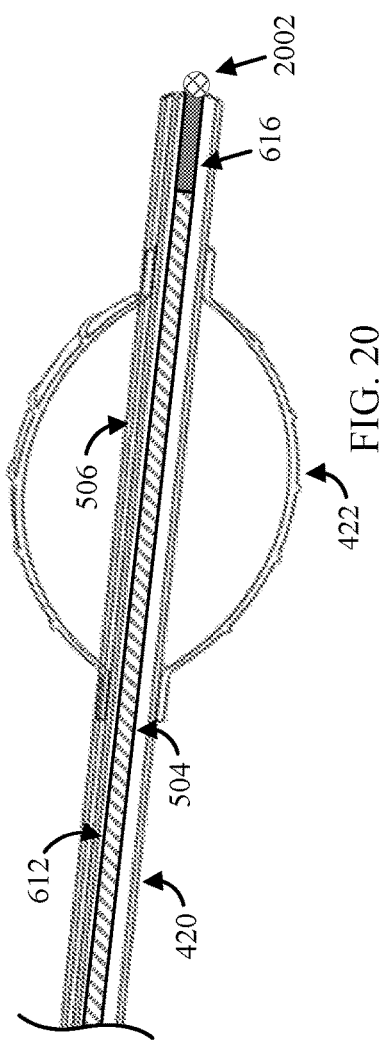
FIG. 20 shows sensing probe access of the GI tract through the TNIT.
Figure 21:
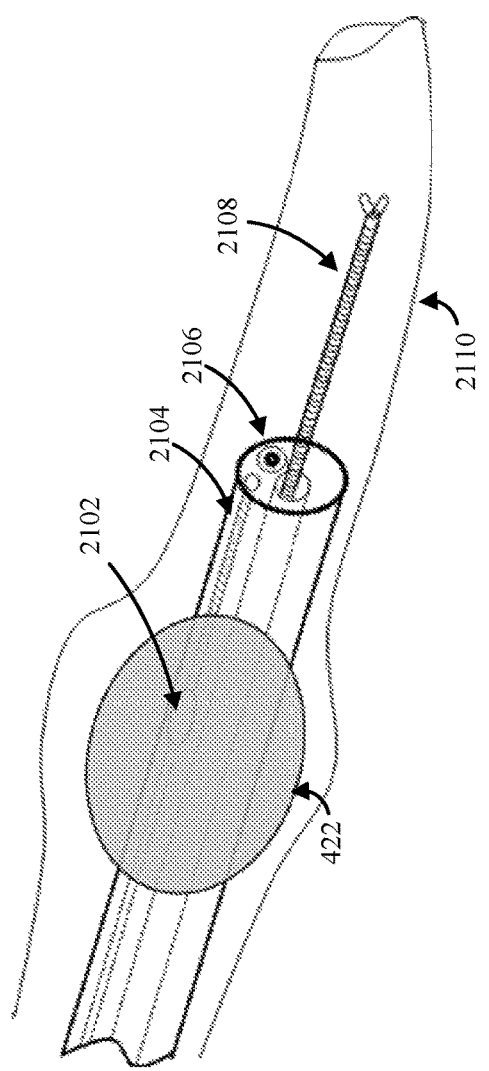
FIG. 21 shows biopsy forceps extending through the TNIT.
Figure 22:
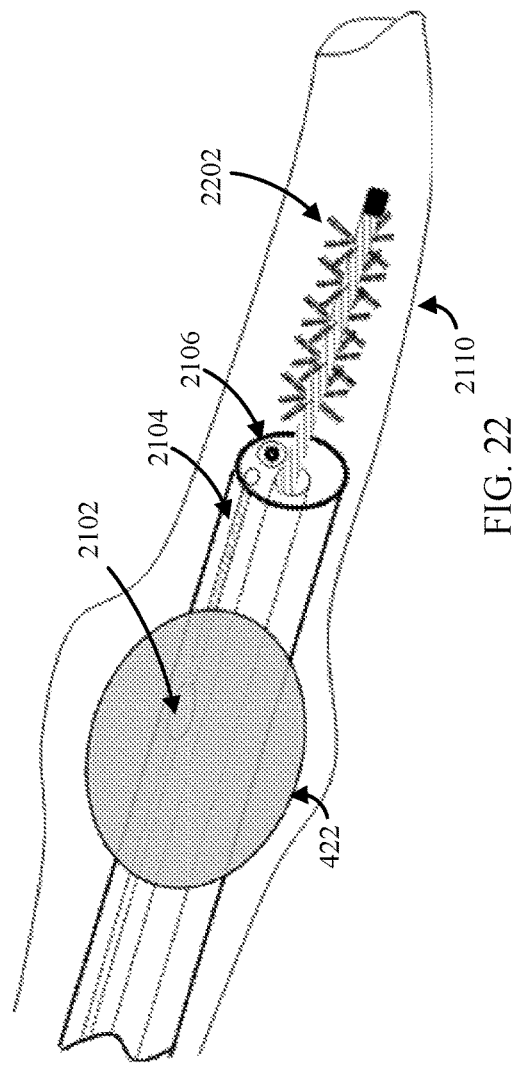
FIG. 22 shows a biopsy brush collecting samples through the TNIT.
Figure 23:
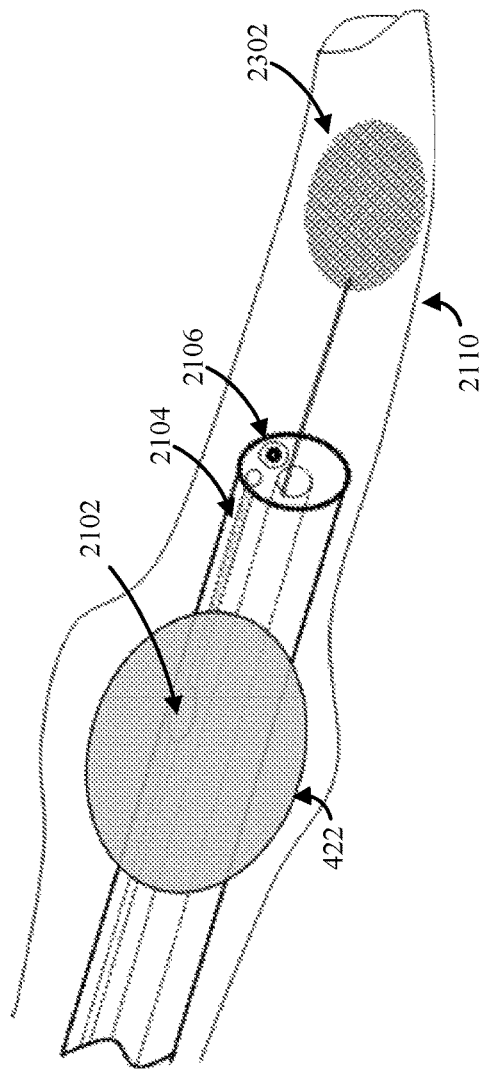
FIG. 23 shows a Cytosponge collecting samples through the TNIT.
Figure 24:
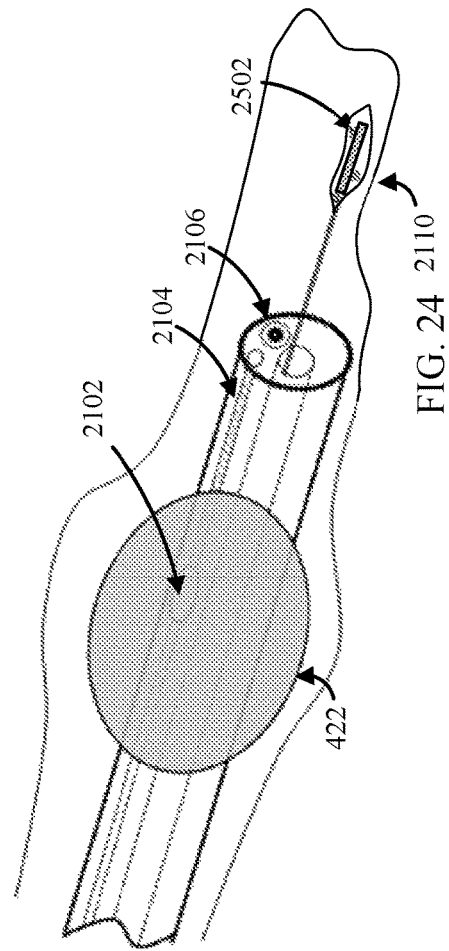
FIG. 24 shows a cryo-biopsy probe obtaining a biopsy through the TNIT.

A sensor probe could be used through the TNIT to monitor several physiological parameters of the GI tract, such as relative gas composition, temperature, or pH of fluids (FIG. 20, showing sensor 2002).

Sampling/Biopsy

Sampling and/or biopsy of the GI tract may be performed through the TNIT in a less invasive way compared to the known procedures. Different sampling probes can be inserted via the TNIT out through the distal end to the GI tract to obtain biopsies which could then be retracted through the working channel. This offers the advantage of obtaining multiple samples from either one or multiple locations in the GI tract. The TNIT can comprise of double lumen, for balloon inflation and sampling. It can also have an extra lumen for a camera or one of the imaging probes mentioned above for guidance. Sampling of gastric juice or bile can be performed through the inner lumen with or without an accessory tube. FIGS. 21-25 show various sampling/biopsy probes and also show the inflatable chamber 422 adjacent to a high-density liquid channel 2104 with an opening 2102 through which high-density liquid may enter and exit the inflatable chamber 422. The portion of the high-density liquid channel 2104 distal to the opening 2102 may be blocked (e.g. with epoxy or other material) to prevent high-density liquid from escaping from the end of the channel 2104. In the embodiment shown in FIGS. 21-25, the TNIT includes a second instrument channel 2106 into which an imaging probe is inserted for monitoring/viewing the biopsy/sampling procedure.

Forceps

Biopsy forceps 2108 can be inserted through the working channel of the TNIT (FIG. 21) to obtain samples from the GI tract (e.g. intestinal wall 2110) with or without guidance from an imaging probe, which may be inserted through an auxiliary channel 2106 in the TNIT.

Biopsy Brush and Cytosponge

A biopsy brush 2202 (FIG. 22) or Cytosponge 2302 (FIG. 23) can also be inserted through the TNIT working channel and rubbed against the mucosal wall of the GI tract. This allows for comprehensive sampling of sections of the GI tract. The Cytosponge can also be employed to sample gastric juice and bile for microbiome and molecular assays.

Cryobiopsy

A cryobiopsy device 2502 that captures tissue by cryoadhesion can be inserted through the working channel of TNIT (FIG. 24) to sample an area of interest 2110 of the GI tract. An imaging probe may be used in an auxiliary channel 2106 of the TNIT to guide the biopsy sampling.

Suction Sampling

Figure 25:
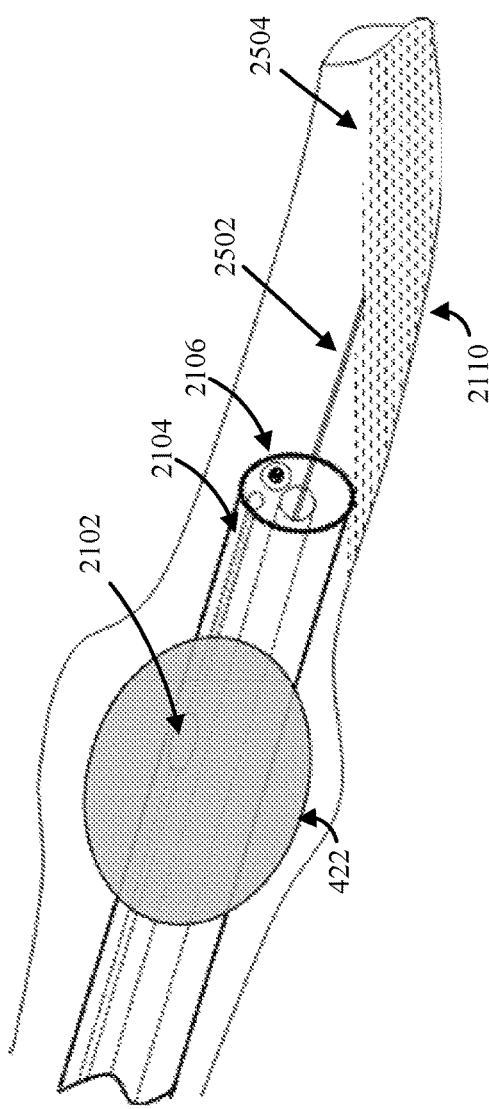
FIG. 25 shows suction sampling being performed through the TNIT probe using a separate suction tube, although in various embodiments the working channel of the TNIT tubing itself may be used to perform suction without the use of a separate suction tube.

The TNIT can be used to obtain samples of gastric juice or bile 2504 with or without any accessory devices. This could be done by applying negative pressure in the working channel or by using an independent suction tubing 2502 through the working channel (FIG. 25).

Treatment

Similar to standard of care endoscopy, treatment can also be performed through the TNIT. This allows for a localized treatment of the GI tract in a minimally invasive fashion. Imaging guidance through an auxiliary channel could be employed for precise selection of the area of interest.

Feeding and Drug Delivery

Figure 26:
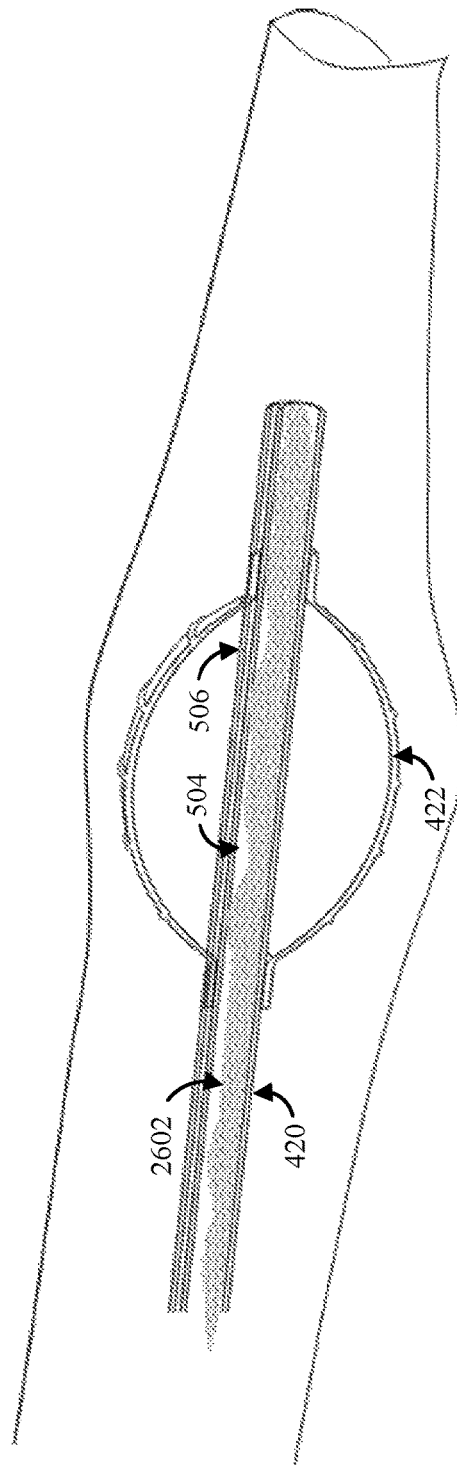
FIG. 26 shows nutrients being introduced into the GI tract through the TNIT.
Figure 27:
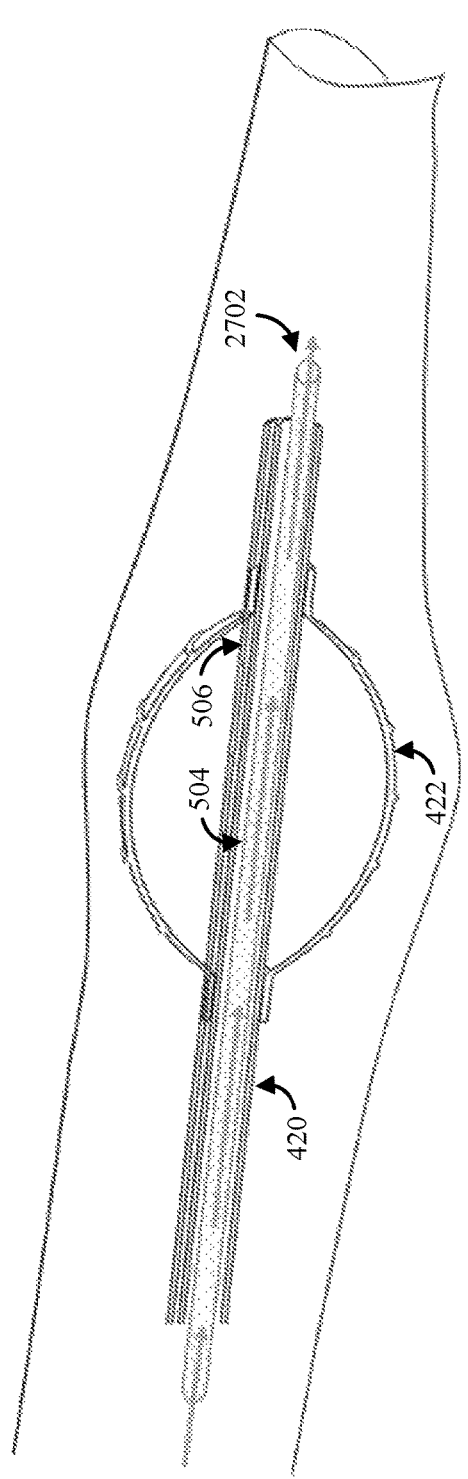
FIG. 27 shows a drug or sensor being inserted into the GI tract through the TNIT.

The working channel of the TNIT may be used to deliver vital nutrients 2602 (FIG. 26) or drugs or other sensors 2702 (FIG. 27) directly into the stomach or small intestine.

Cautery, Cryoablation, and Radiofrequency Ablation

Figure 28A:
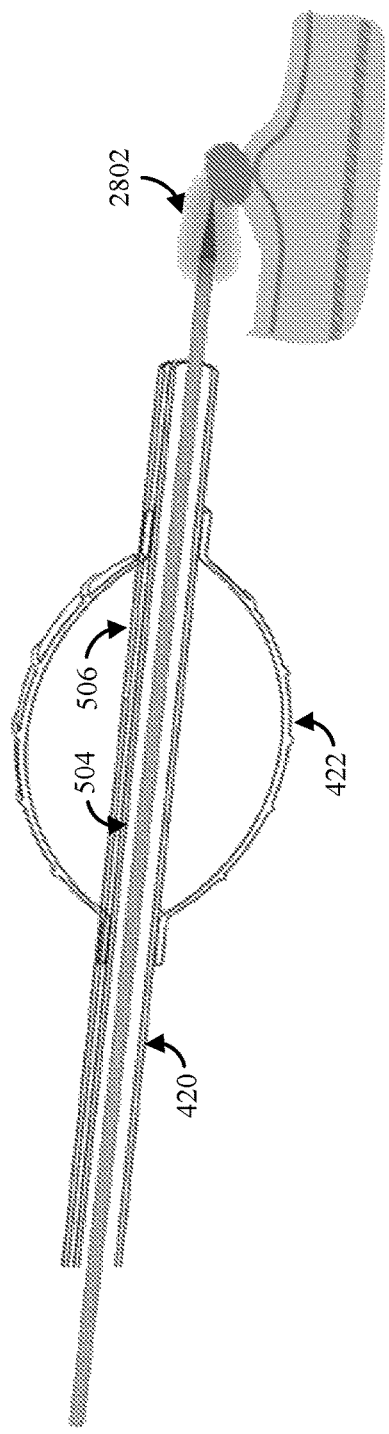
FIG. 28A shows a cautery probe and FIG. 28B shows an electrocautery probe being inserted through the TNIT.
Figure 28B:
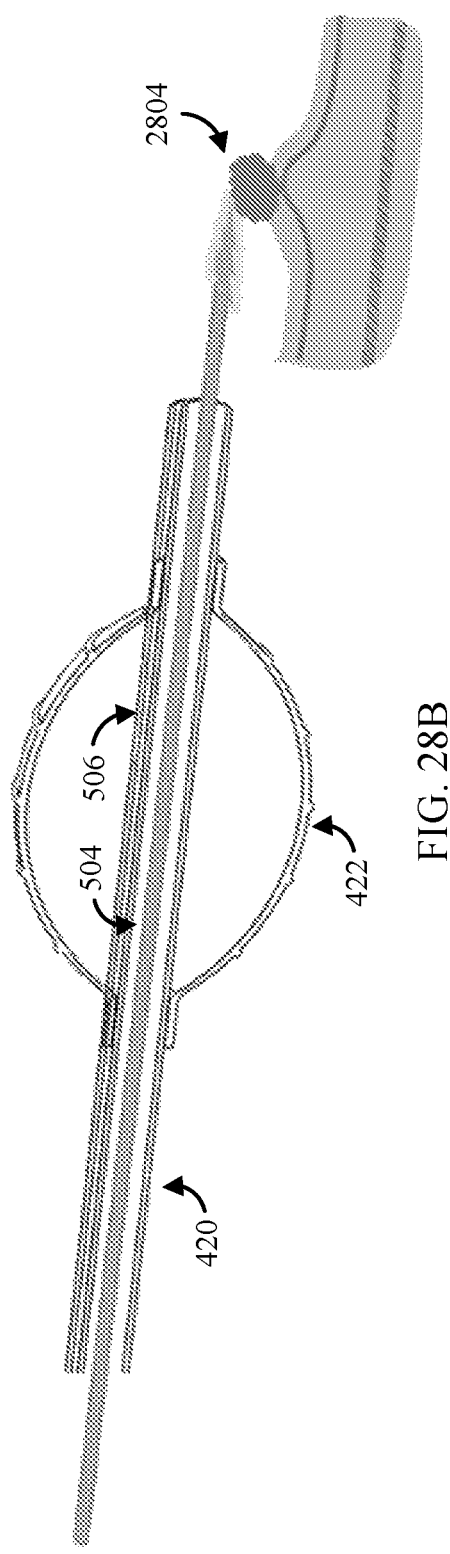
Figure 29:
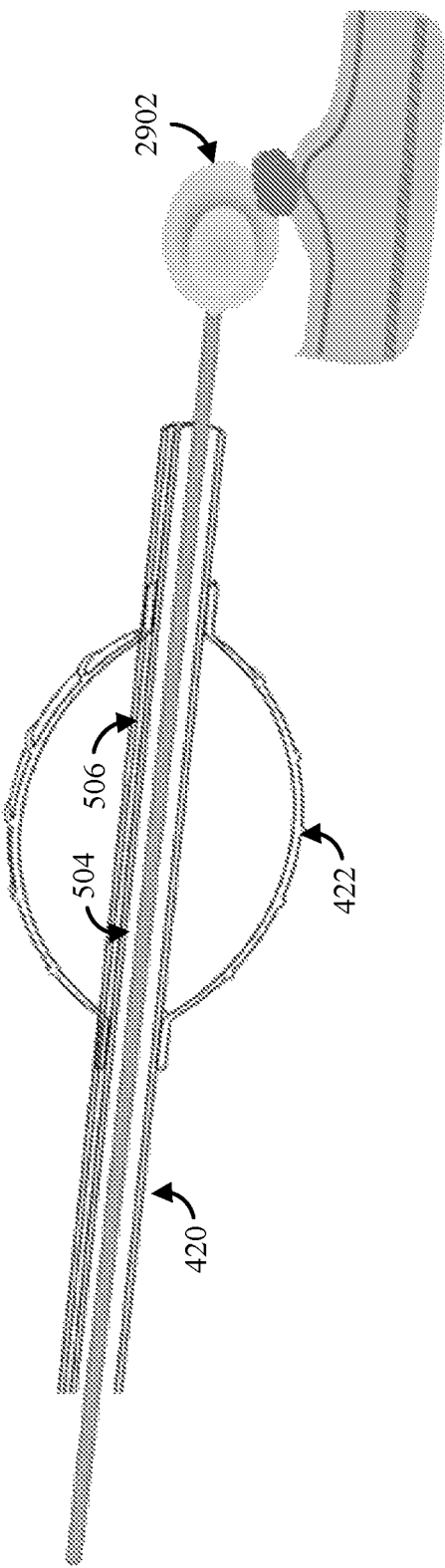
FIG. 29 shows a cryoablation probe being inserted through the TNIT.
Figure 30:
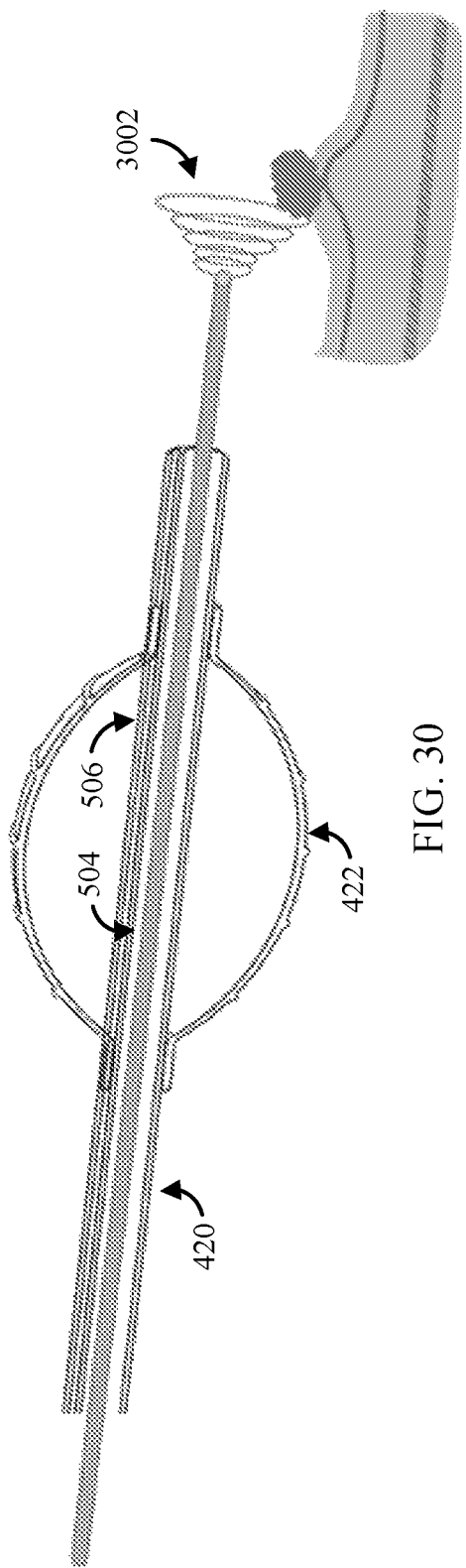
FIG. 30 shows a radiofrequency ablation probe being inserted through the TNIT.

A cautery 2802 (FIG. 28A), electrocautery 2804 (FIG. 28B), cryoablation 2902 (FIG. 29), or radiofrequency ablation device 3002 (FIG. 30) can be inserted into the working channel of the TNIT to induce necrosis of diseased tissue. Imaging guidance through an auxiliary channel could be employed for precise selection of the area of interest.

Foreign Body Retrieval

Figure 31:
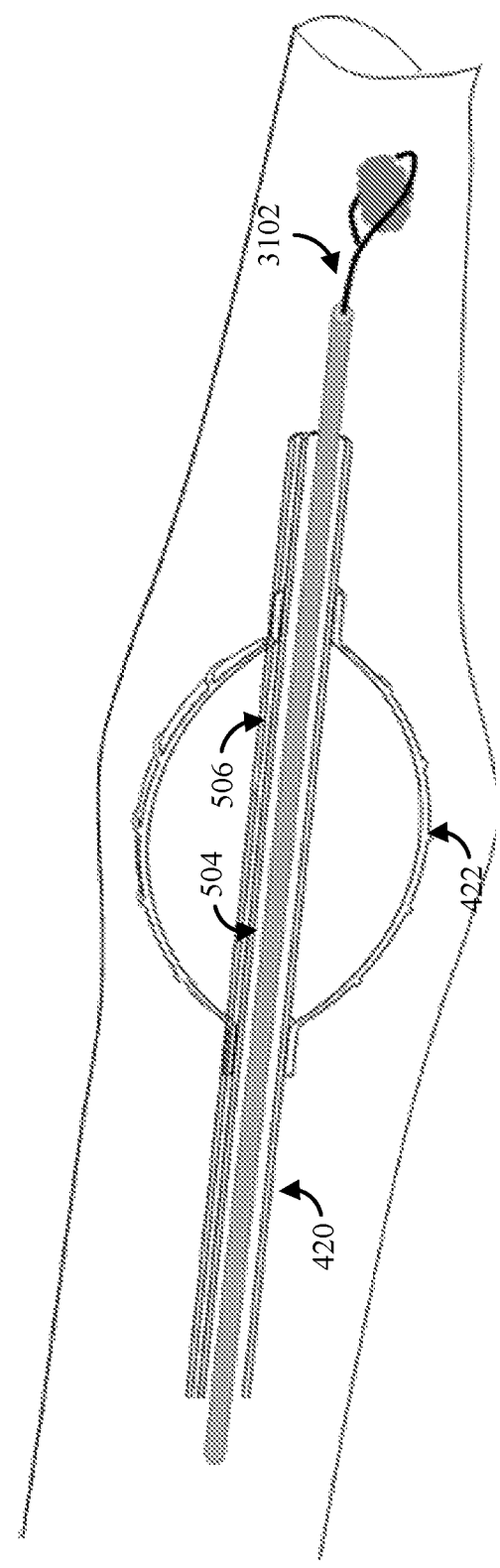
FIG. 31 shows a foreign body being retrieved through the TNIT.

Snares, a Roth net, or similar devices 3102 can be introduced through the working channel of the TNIT for foreign body retrieval (FIG. 31). Imaging guidance through an auxiliary channel (see FIGS. 21-25) could be employed for precise selection of the area of interest.

Photodynamic Therapy and Photothermal Therapy

A light guide medium such as an optical fiber can be inserted into the working channel of TNIT to conduct light-enabled therapy, like photodynamic therapy (FIG. 32, showing photodynamic therapy probe 3202) and photothermal therapy (FIG. 33, showing photothermal therapy probe 3302). Another channel or lumen of the TNIT (when present; see FIGS. 21-25) can also be used when the exogenous agent like photosensitizer needs to be introduced in situ.

Endoscopic Mucosal Resection (EMR)/Endoscopic Submucosal Dissection (ESD)

Figure 34:
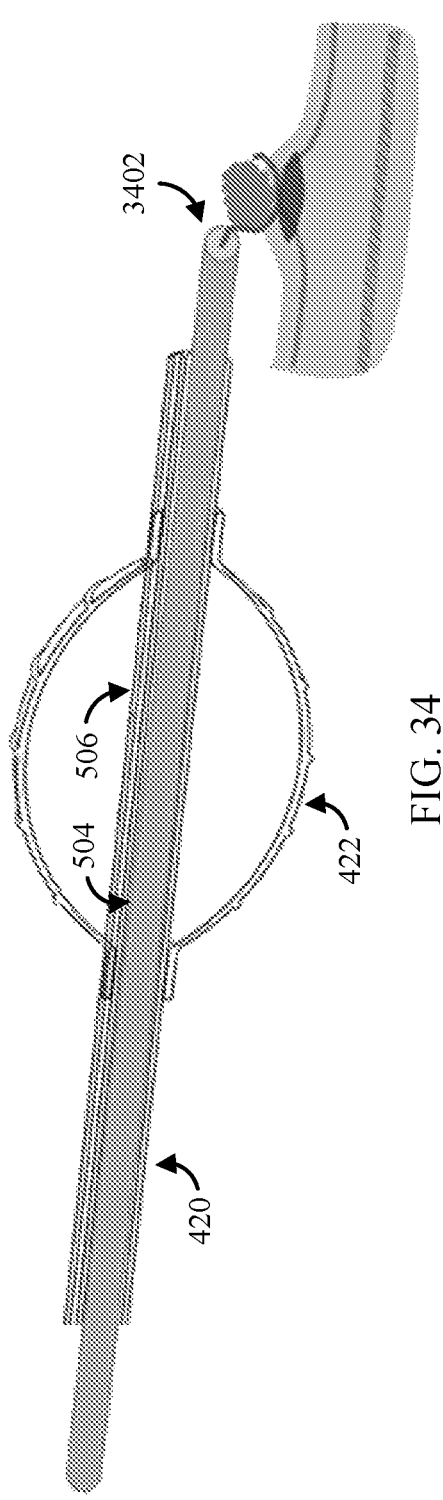
FIG. 34 shows endoscopic mucosal resection (EMR) being performed through the TNIT.
Figure 35:
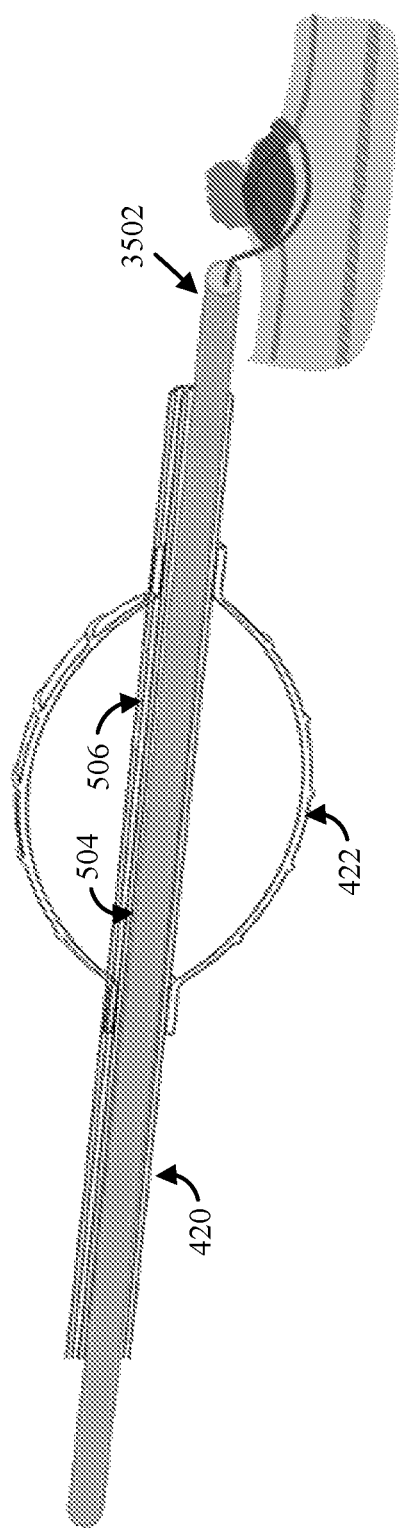
FIG. 35 shows endoscopic submucosal dissection (ESD) being performed through the TNIT.

Endoscopic mucosal resection (EMR) (FIG. 34, showing EMR probe 3402) or endoscopic submucosal dissection (ESD) (FIG. 35, showing ESD probe 3502), which are two common treatments in GI tract that are conducted via an endoscope and which may also be performed via the working channel of the TNIT to enable superficial layer lesion treatment or en bloc resection of deeper lesions.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

What is claimed is:

1. A catheter, comprising:
an elongated tube having a first channel and a second channel, wherein the elongated tube has a length that facilitates transnasal insertion into a subject's duodenum;
an inflatable chamber coupled to the elongated tube and in fluid communication with the first channel,
the inflatable chamber in a deflated state having a diameter equal to a diameter of the elongated tube; and
a high-density liquid delivery system in fluid communication with the first channel,
the high-density liquid delivery system delivering a high-density liquid to the inflatable chamber via the first channel to cause the inflatable chamber to expand, and
the inflatable chamber in an inflated state having a mass of at least 3.0 grams such that the high-density liquid-filled inflatable chamber is configured to advance to the subject's duodenum under force of gravity; and
the second channel having a circular cross-section, wherein the second channel has a biopsy probe disposed therein, the biopsy probe projecting beyond the distal end of the elongated tube, wherein the biopsy probe obtains a sample cryogenically.

2. The catheter of claim 1, wherein the high-density liquid has a density of at least 2 g/cm$^3$.

3. The catheter of claim 1, wherein the elongated tube includes a third channel.

4. The catheter of claim 3, further comprising an optical fiber disposed within the second or third channel, wherein a distal end of the optical fiber comprises an optical probe extending through the inflatable chamber and projecting beyond a distal end of the elongated tube.

5. A method, comprising:
  providing a catheter comprising:
    an elongated tube having a first channel and a second channel, wherein the elongated tube has a length that facilitates transnasal insertion into a subject's duodenum,
    an inflatable chamber coupled to the elongated tube and in fluid communication with the first channel,
      the inflatable chamber in a deflated state having a diameter equal to a diameter of the elongated tube, and
      the inflatable chamber in an inflated state having a mass of at least 3.0 grams, and
    a high-density liquid delivery system in fluid communication with the first channel;
  delivering, using the high-density liquid delivery system, a high-density liquid to the inflatable chamber via the first channel to cause the inflatable chamber to expand; and
  advancing the high-density liquid-filled inflatable chamber to the subject's duodenum under force of gravity; and
  delivering the high-density liquid to the inflatable chamber via the first channel to cause the inflatable chamber to expand when the inflatable chamber is in the subject's stomach or other gastrointestinal space.

6. The method of claim 5, wherein the high-density liquid has a density of at least 2 $g/cm^3$.

7. A catheter, comprising:
  an elongated tube having a first channel and a second channel, wherein the elongated tube has a length that facilitates transnasal insertion into a subject's duodenum;
  an inflatable chamber coupled to the elongated tube and in fluid communication with the first channel,
    the inflatable chamber in a deflated state having a diameter equal to a diameter of the elongated tube; and
    a high-density liquid delivery system in fluid communication with the first channel,
    the high-density liquid delivery system delivering a high-density liquid to the inflatable chamber via the first channel to cause the inflatable chamber to expand, and
    the inflatable chamber in an inflated state having a mass of at least 3.0 grams such that the high-density liquid-filled inflatable chamber is configured to advance to the subject's duodenum under force of gravity;
  the second channel has a substantially circular cross-section, wherein the second channel has a biopsy probe disposed therein, the biopsy probe projecting beyond the distal end of the elongated tube, wherein the biopsy probe obtains a biopsy sample cryogenically.

8. The catheter of claim 7, wherein the high-density liquid has a density of at least 2 $g/cm^3$.

9. The catheter of claim 7, wherein the catheter further comprising an optical fiber disposed within the second channel, wherein a distal end of the optical fiber comprises an optical probe extending through the inflatable chamber and projecting beyond a distal end of the elongated tube.

10. The catheter of claim 9, wherein the optical fiber is rotatably disposed within the second channel.

11. The catheter of claim 7, wherein the biopsy probe comprises an optical fiber, and wherein the optical fiber emits an optical beam to determine when the biopsy probe is in contact with a tissue.

12. The catheter of claim 7, wherein the second channel has a treatment probe disposed therein.

13. The catheter of claim 12, wherein the treatment probe is configured to perform at least one of: feeding, drug delivery, cautery, electrocautery, cryoablation, radiofrequency ablation, foreign body retrieval, photodynamic therapy, photothermal therapy, Endoscopic mucosal resection (EMR), or endoscopic submucosal dissection (ESD).

14. The catheter of claim 7, wherein the second channel has a diagnostic probe disposed therein.

15. The catheter of claim 14, wherein the diagnostic probe includes at least one of: an optical coherence tomography probe, a spectrally encoded confocal microscopy probe, a narrow band imaging probe, a white light imaging probe, a near infrared spectroscopy probe, a Raman spectroscopy probe, a fluorescence imaging probe, or a gas/temperature/pH sensor probe.

16. A transnasal introduction tube, comprising:
  an elongated tube having a maximum exterior diameter in a range from 6 French to 9 French, the elongated tube having a length that facilitates transnasal insertion into a subject's duodenum, and the elongated tube comprising:
    a first channel having a circular cross-section with a first inner diameter; and
    a second channel having a circular cross-section with a second inner diameter that is narrower than the first inner diameter;
  a biopsy probe disposed within the first channel, wherein the biopsy probe obtains a sample cryogenically;
  a third channel;
  an inflatable chamber coupled to the elongated tube and in fluid communication with the third channel,
    the inflatable chamber in a deflated state having a diameter equal to a diameter of the elongated tube; and
  a high-density liquid delivery system in fluid communication with the third channel,
    the high-density liquid delivery system delivering a high-density liquid to the inflatable chamber via the third channel to cause the inflatable chamber to expand, and
    the inflatable chamber in an inflated state having a mass of at least 3.0 grams such that the high-density liquid-filled inflatable chamber is configured to advance to the subject's duodenum under force of gravity.

17. The transnasal introduction tube of claim 16, wherein the high-density liquid has a density of at least 2 $g/cm^3$.

18. The transnasal introduction tube of claim 16, further comprising an optical fiber disposed within the second channel, wherein the optical fiber projects beyond a distal end of the transnasal introduction tube.

19. The transnasal introduction tube of claim 18, wherein the optical fiber is rotatably disposed within the second channel.

20. The transnasal introduction tube of claim 16, wherein the biopsy probe comprises an optical fiber, and wherein the optical fiber emits an optical beam to determine when the biopsy probe is in contact with a tissue.

21. The transnasal introduction tube of claim 16, further comprising a treatment probe configured to perform at least one of: feeding, drug delivery, cautery, electrocautery, cryoablation, radiofrequency ablation, foreign body retrieval, photodynamic therapy, photothermal therapy, Endoscopic mucosal resection (EMR), or endoscopic submucosal dissection (ESD).

22. The transnasal introduction tube of claim 16, further comprising a diagnostic probe that includes at least one of: an optical coherence tomography probe, a spectrally encoded confocal microscopy probe, a narrow band imaging probe, a white light imaging probe, a near infrared spectroscopy probe, a Raman spectroscopy probe, a fluorescence imaging probe, or a gas/temperature/pH sensor probe.

* * * * *